(12) United States Patent
Constantineau et al.

(10) Patent No.: US 11,154,658 B2
(45) Date of Patent: Oct. 26, 2021

(54) MIXING AND INJECTION DEVICE WITH STERILITY FEATURES

(71) Applicant: Wingap Medical, Inc., Watertown, MA (US)

(72) Inventors: Cole Constantineau, Cambridge, MA (US); Adam R Standley, Boston, MA (US); Jeffrey Thomas Chagnon, Somerville, MA (US)

(73) Assignee: Windgap Medical, Inc, Watertown, MA (US)

( * ) Notice: Subject to any disclaimer, the term of this patent is extended or adjusted under 35 U.S.C. 154(b) by 265 days.

(21) Appl. No.: 16/293,127

(22) Filed: Mar. 5, 2019

(65) Prior Publication Data

US 2019/0240407 A1 Aug. 8, 2019

Related U.S. Application Data

(63) Continuation of application No. 15/313,294, filed as application No. PCT/US2016/047023 on Aug. 15, 2016, now Pat. No. 10,220,147.

(Continued)

(51) Int. Cl.
*A61M 5/19* (2006.01)
*A61M 5/20* (2006.01)
(Continued)

(52) U.S. Cl.
CPC .............. *A61M 5/19* (2013.01); *A61J 1/1406* (2013.01); *A61J 1/2096* (2013.01);
(Continued)

(58) Field of Classification Search
CPC ........ A61J 1/05; A61J 1/20; A61J 1/14; A61J 1/1406; A61J 1/2096; A61M 2005/2013;
(Continued)

(56) References Cited

U.S. PATENT DOCUMENTS

| | | | |
|---|---|---|---|
| 6,743,203 B1 * | 6/2004 | Pickhard | A61M 5/2033 604/139 |
| 2008/0183140 A1 * | 7/2008 | Paproski | A61M 5/326 604/232 |

(Continued)

FOREIGN PATENT DOCUMENTS

| | | | | |
|---|---|---|---|---|
| WO | WO-2011060541 A1 * | 5/2011 | | A61M 5/285 |
| WO | WO-2014080020 A1 * | 5/2014 | | B65B 3/003 |
| WO | WO-2014195183 A1 * | 12/2014 | | A61M 5/3245 |

*Primary Examiner* — Jason E Flick
(74) *Attorney, Agent, or Firm* — Ascentage Patent Law, LLC; Travis Lee Johnson

(57) ABSTRACT

The present invention relates to a mixing and injector device which can include: a housing having a plurality of separate and distinct chambers disposed therein; one or more displacement mechanisms corresponding to each of the plurality of chambers disposed within the housing; a needle assembly being provided about one of the plurality of chambers, the needle assembly including the following: a septum; a needle being separated from the plurality of chambers by the septum, the needle having a proximal end configured to pierce the septum in an actuated state; and a needle carrier, the needle carrier being configured to translate axially with respect to and toward the septum and pierce the septum and provide fluid communication from the plurality of chambers through the needle in the actuated state.

20 Claims, 18 Drawing Sheets

Related U.S. Application Data

(60) Provisional application No. 62/204,940, filed on Aug. 13, 2015.

(51) Int. Cl.
*A61M 5/32* (2006.01)
*A61J 1/14* (2006.01)
*A61J 1/20* (2006.01)
*A61M 5/315* (2006.01)
*A61M 5/24* (2006.01)
*A61M 5/31* (2006.01)

(52) U.S. Cl.
CPC ........ *A61M 5/2033* (2013.01); *A61M 5/2066* (2013.01); *A61M 5/31596* (2013.01); *A61M 5/3202* (2013.01); *A61M 5/3243* (2013.01); *A61M 5/326* (2013.01); *A61M 2005/206* (2013.01); *A61M 2005/2013* (2013.01); *A61M 2005/247* (2013.01); *A61M 2005/2451* (2013.01); *A61M 2005/3118* (2013.01)

(58) Field of Classification Search
CPC .... A61M 2005/206; A61M 2005/2451; A61M 2005/247; A61M 2005/3118; A61M 5/19; A61M 5/2033; A61M 5/2066; A61M 5/31596; A61M 5/3202; A61M 5/3243; A61M 5/326; A61M 5/178; A61M 5/20; A61M 5/2448; A61M 5/2445; A61M 5/2466; A61M 2005/3117
See application file for complete search history.

(56) References Cited

U.S. PATENT DOCUMENTS

2012/0302989 A1* 11/2012 Kramer ............... A61M 5/2466 604/500
2013/0110049 A1* 5/2013 Cronenberg ...... A61M 5/14248 604/180

* cited by examiner

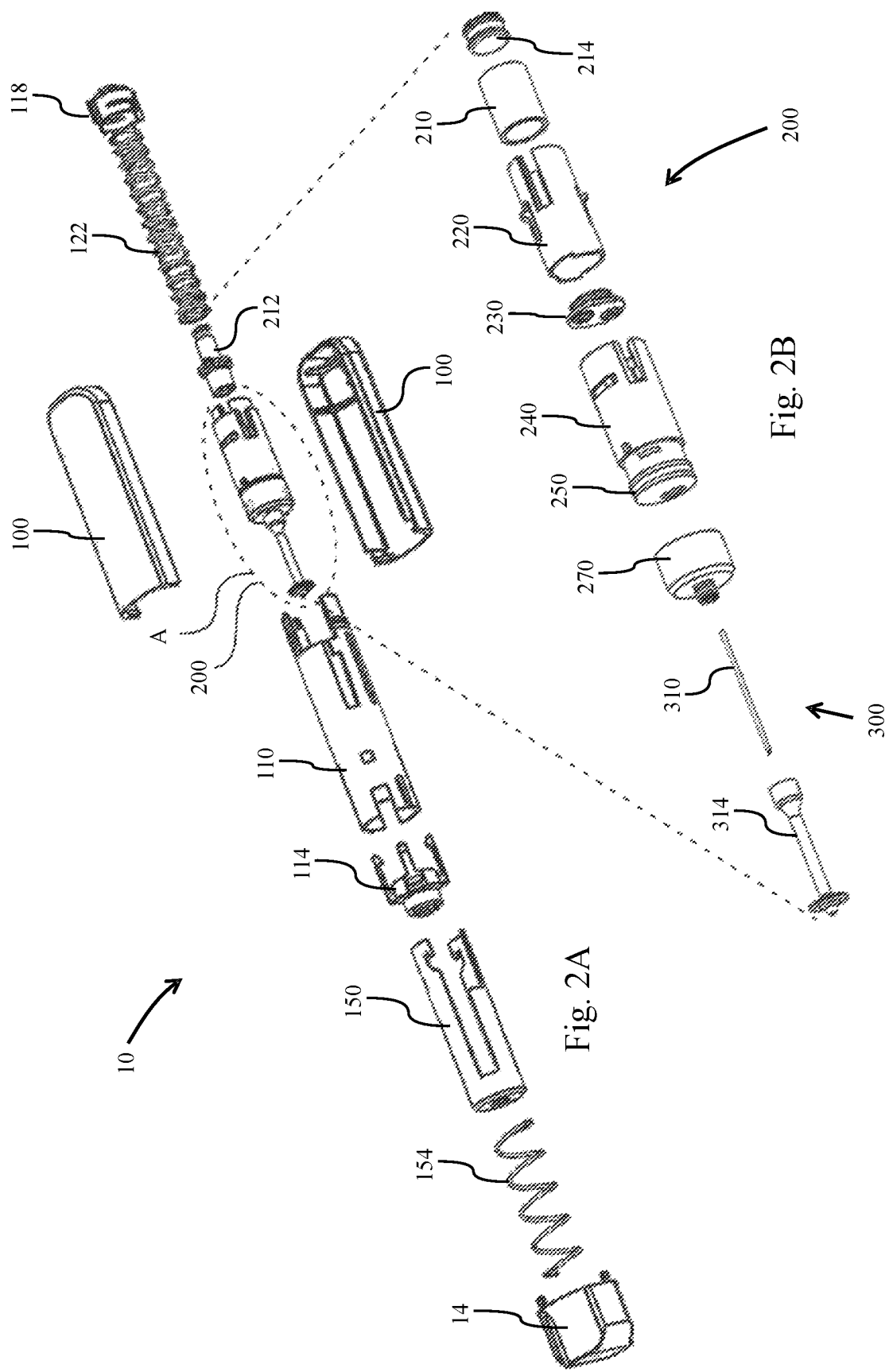

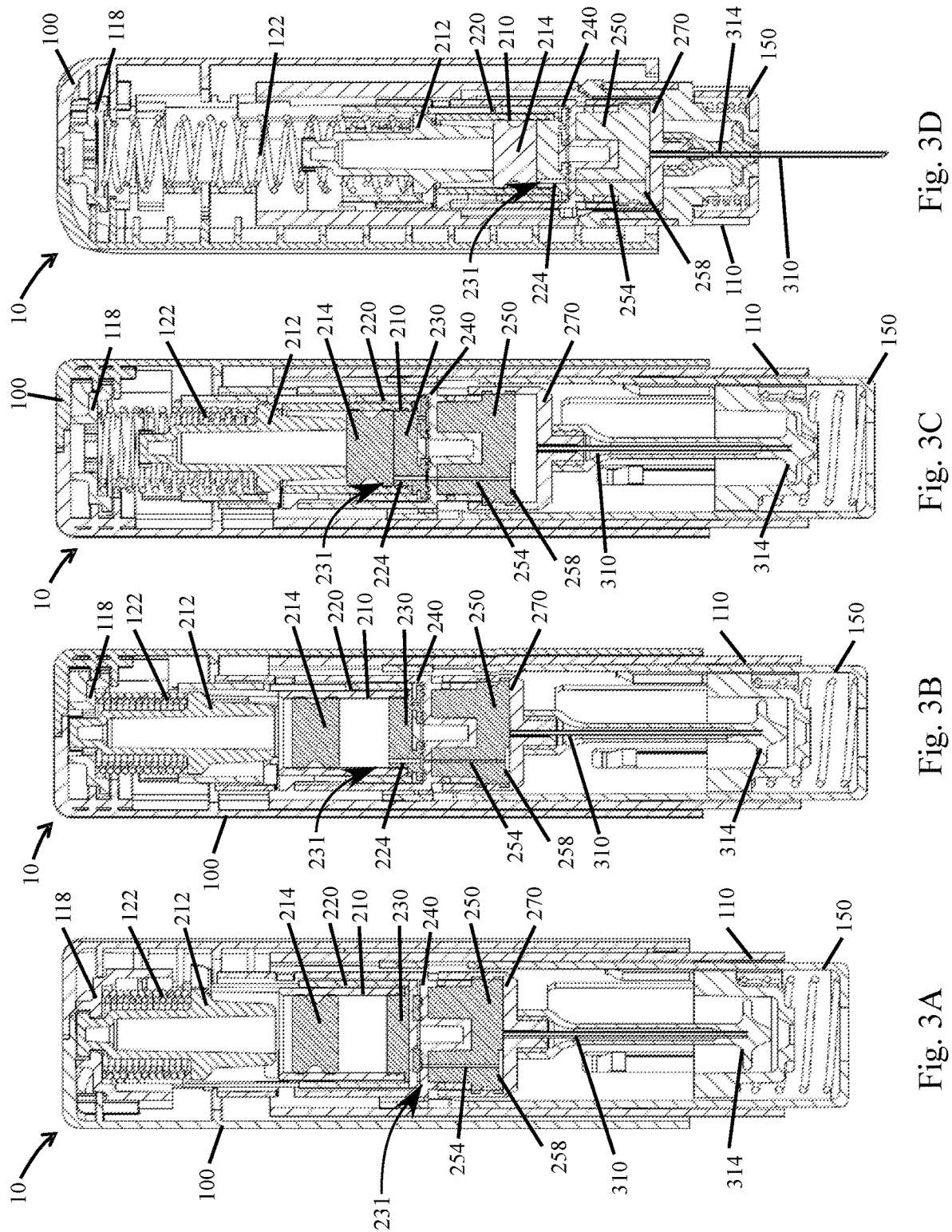

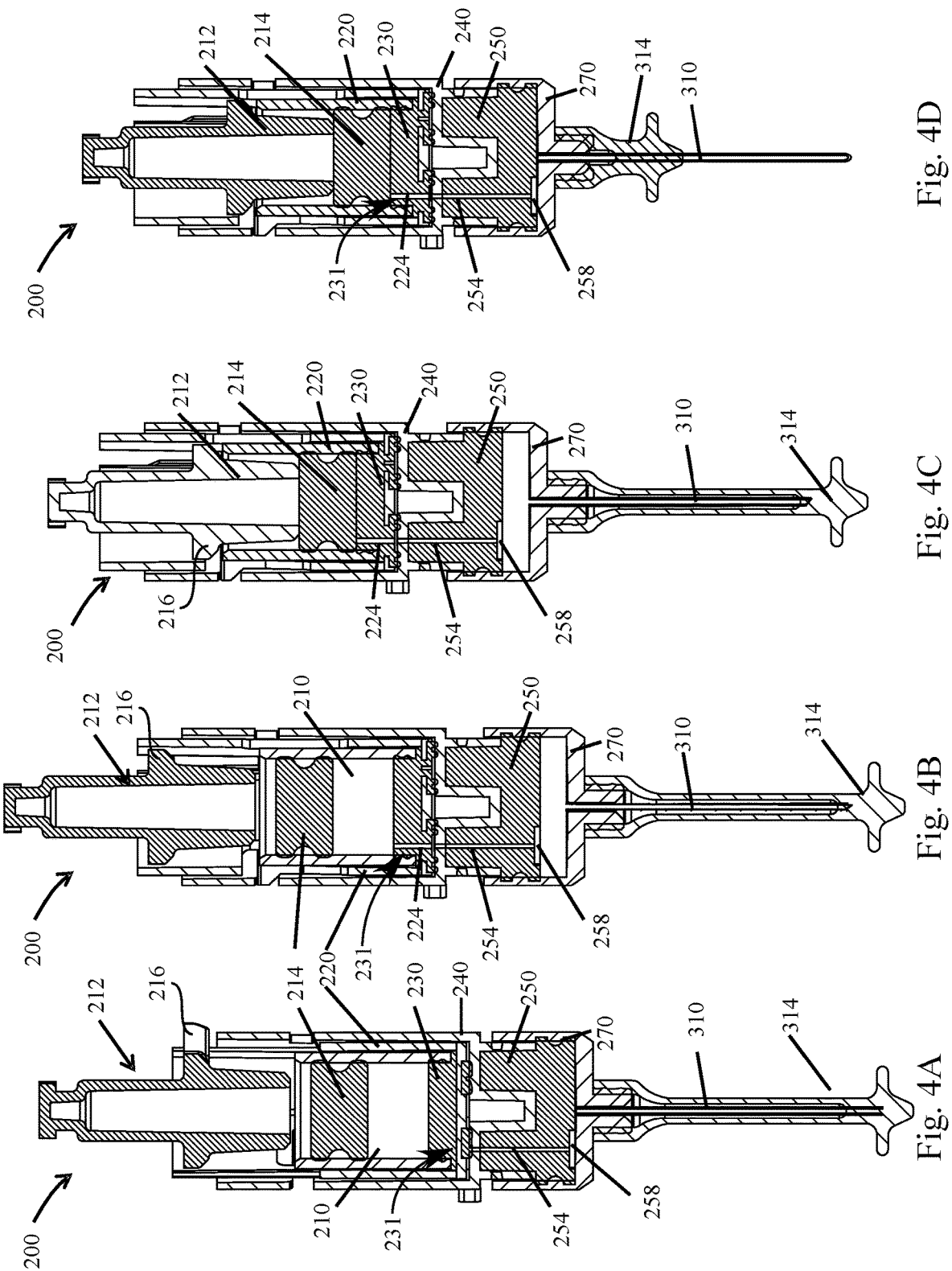

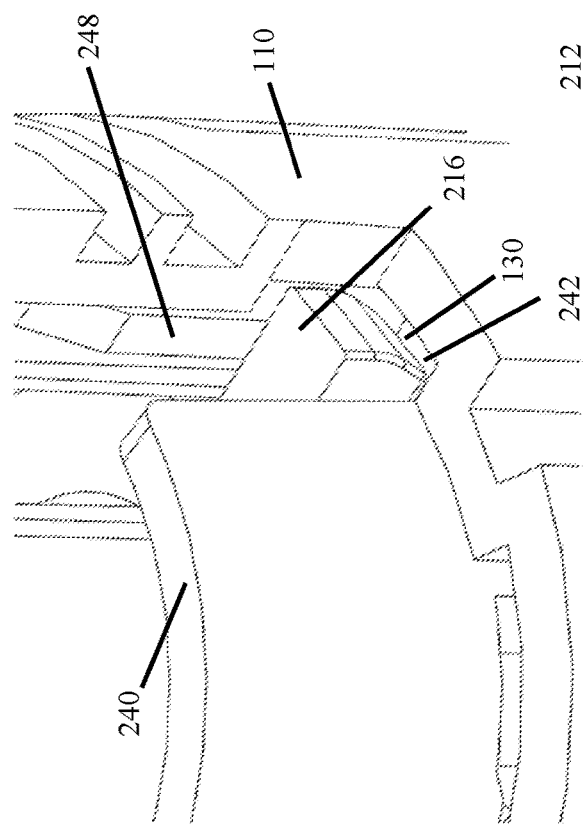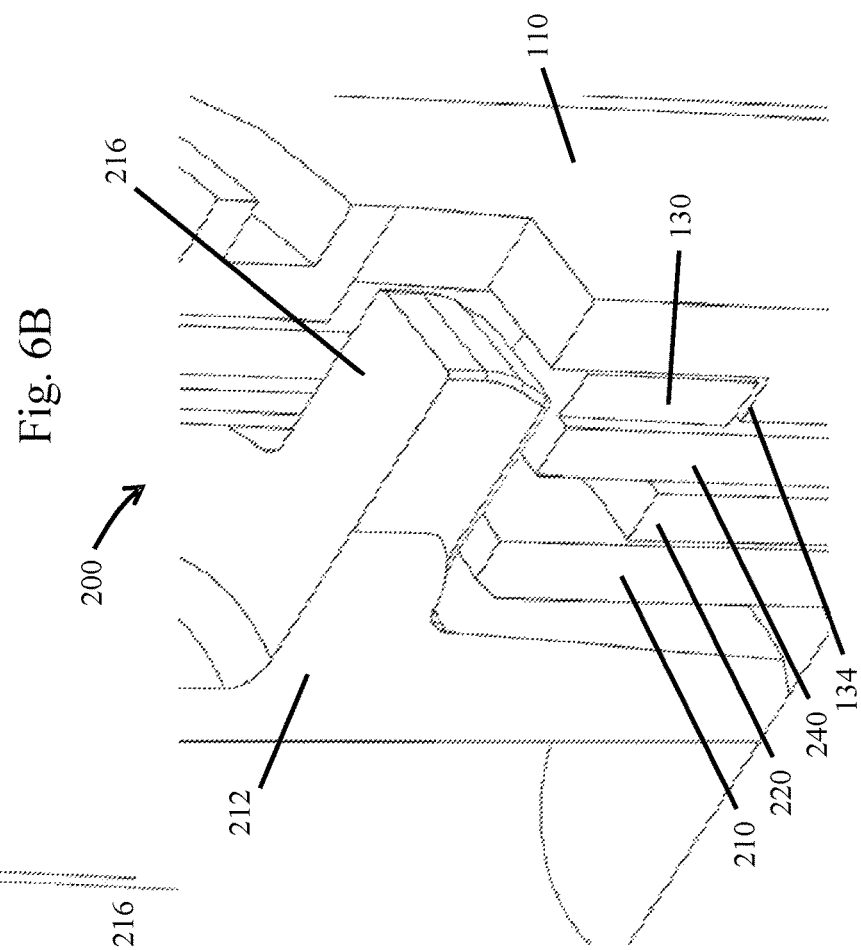
Fig. 6A
Fig. 6B

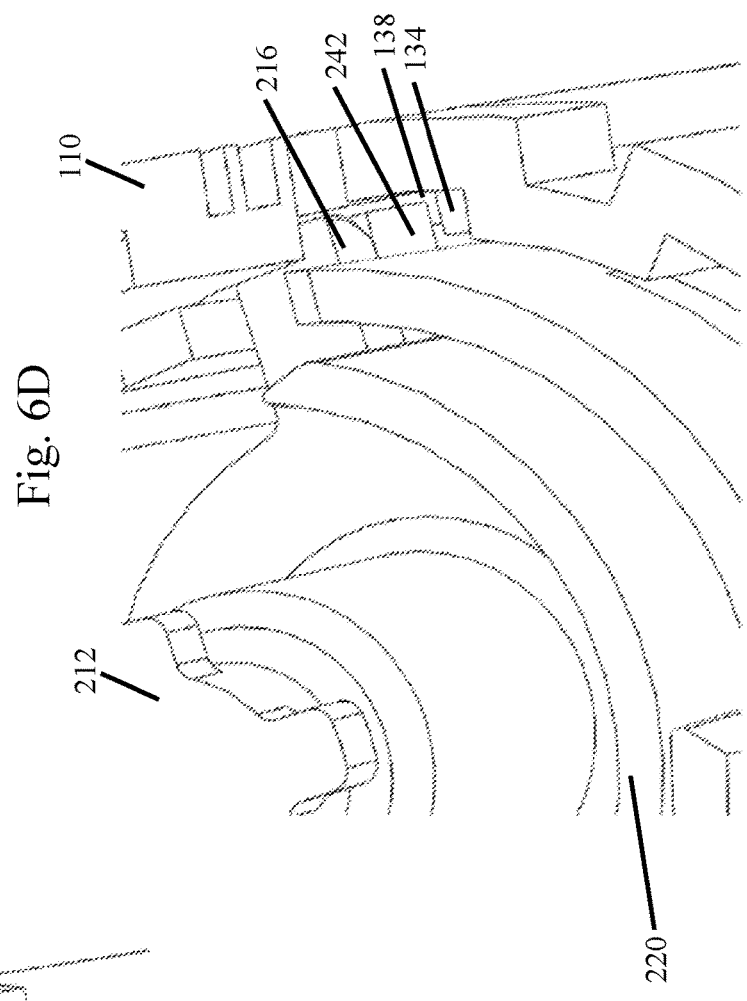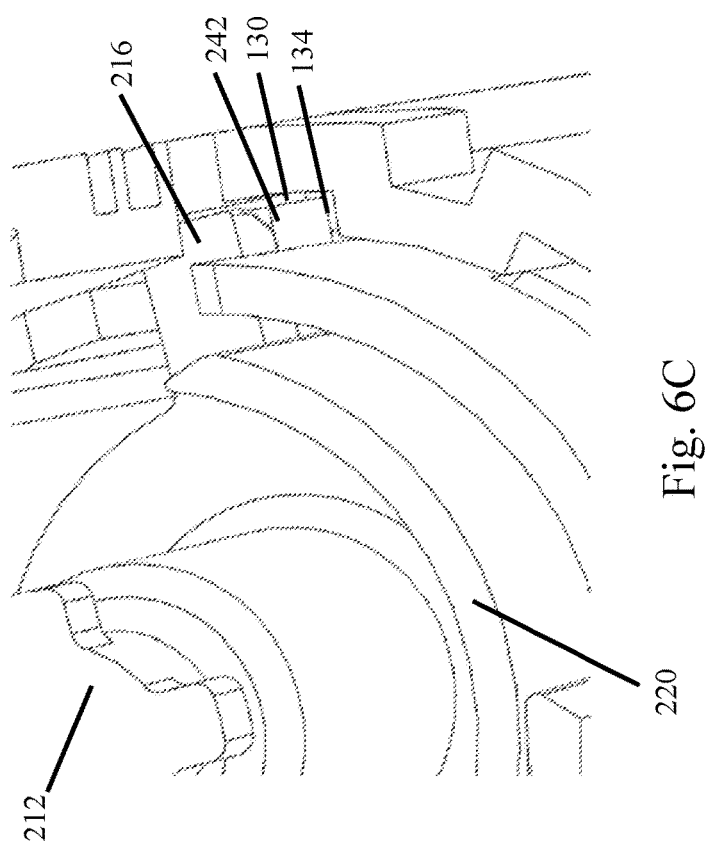

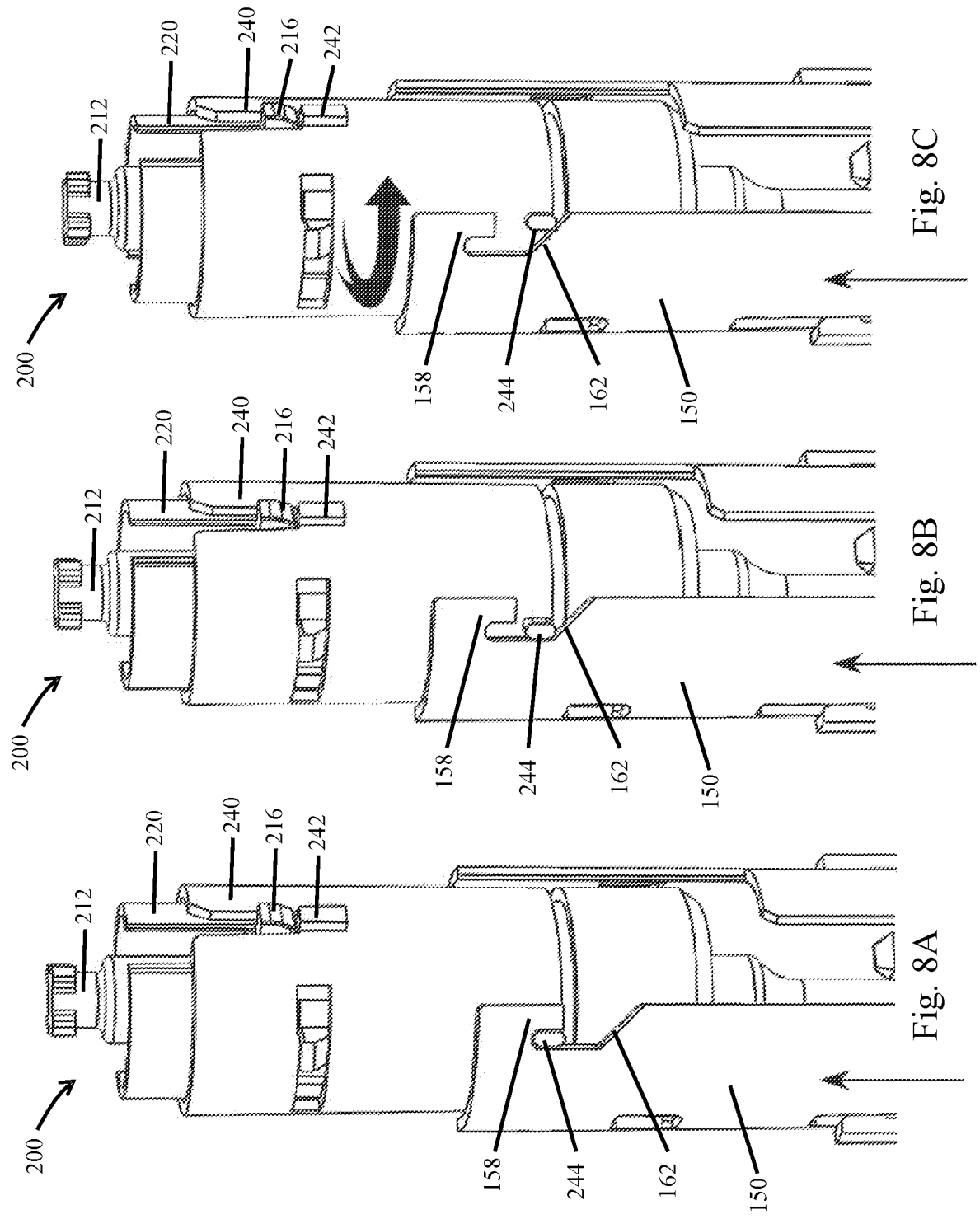

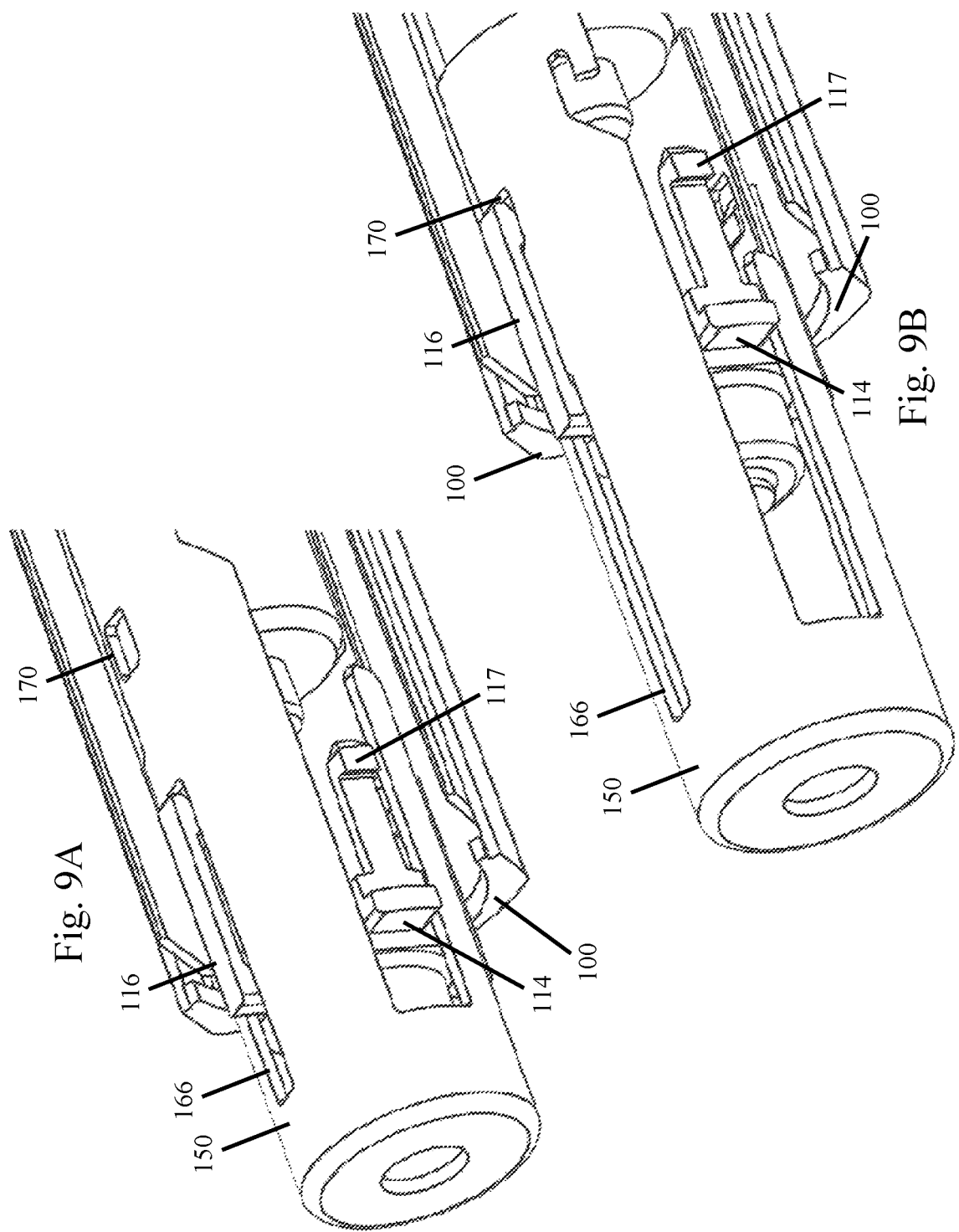

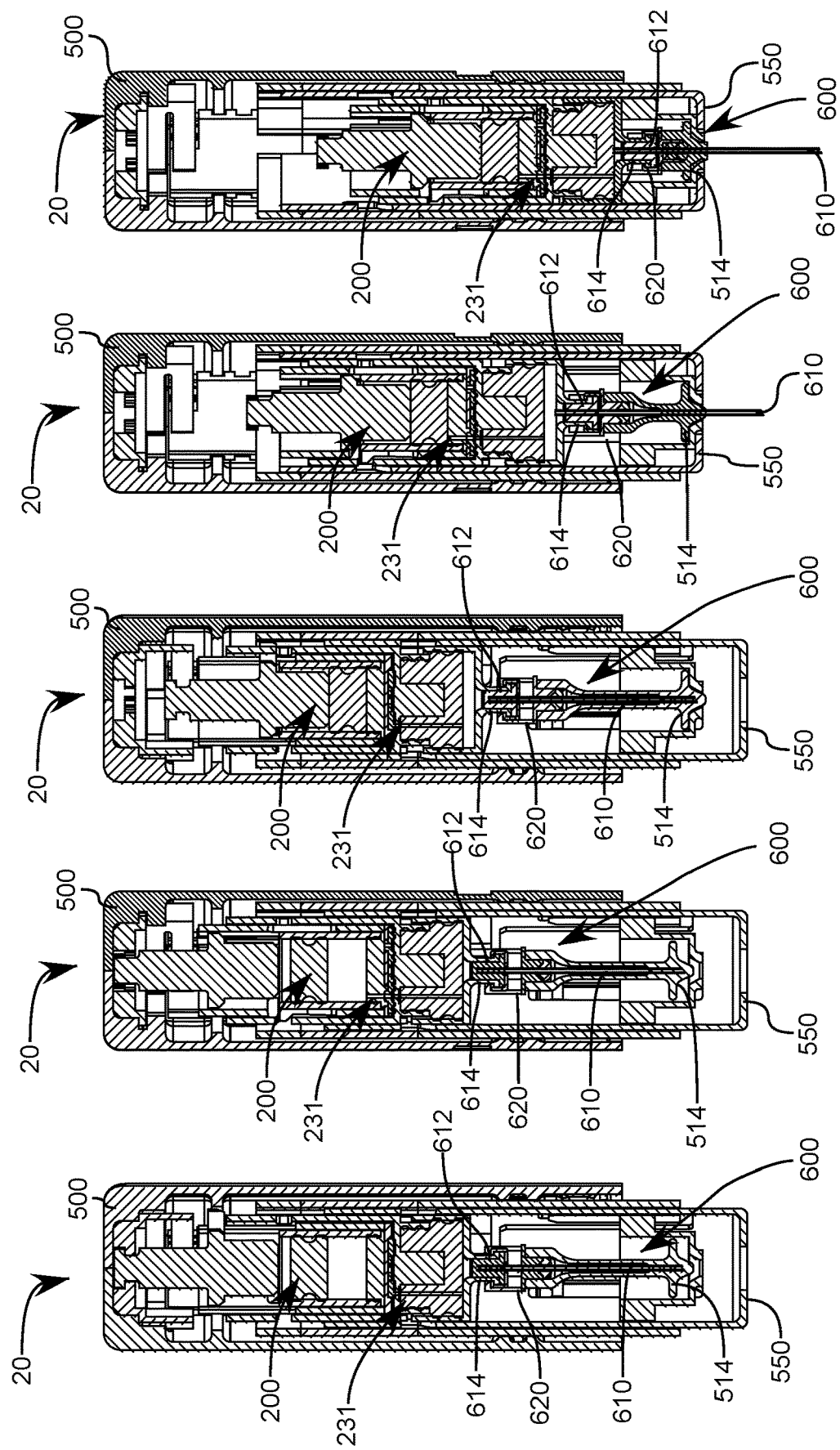

MIXING AND INJECTION DEVICE WITH STERILITY FEATURES

CROSS-REFERENCE TO RELATED APPLICATIONS

This application claims the benefit of Pending application Ser. No. 15/313,294 filed on Nov. 22, 2016, and which claims the benefit to PCT application number PCT/US16/47023 which was filed on Aug. 15, 2016, and which claims priority to U.S. Patent Application No. 62/204,940 which was filed on Aug. 13, 2015 each of which are herein incorporated by reference in their entirety.

FIELD OF THE INVENTION

The present invention relates generally to auto-injectors and prefilled syringes and more particularly to auto-injectors that store in a compact state and allow for formation or reconstitution of a therapeutic agent for injection.

BACKGROUND OF THE INVENTION

Individuals who suffer from certain medical conditions are often required to keep an auto-injector or prefilled syringe nearby in order to address a medical need. A few examples of this are insulin pens for people with diabetes, epinephrine for those with food and insect stings allergies, and antidotes for soldiers at risk of exposure to chemical and/or biological toxins in the field. For example, an allergic reaction may occur in a location which is physically distant from the nearest hospital or medical facility. For example, bee stings, are more likely to occur outside than indoors. Food containing peanuts are more likely to be supplied to the individual away from a controlled home environment like at a baseball park. Having a portable epinephrine auto-injector nearby enables emergency intervention after an exposure to an allergen.

Size is an issue when it comes to auto-injectors. Many owners of the devices are hesitant to carry their injector with them if it represents a burden, by providing injectors in more compact sizes it will make it more likely that they will.

Shelf-life is also a large issue with respect to auto-injectors, which can be expensive and used fairly infrequently. For example a user who has intense allergic reactions to shellfish can go years between exposures and subsequent injections. In such a case it can be easy to forget to replace the auto-injector after expiration, whereupon in an emergency, the drugs contained therein have expired and are either ineffective or have a greatly reduced effectiveness due to decomposition of the drugs contained therein. As will be appreciated by those having skill in the art, the shelf life can be increased by storing the desired medication in an unmixed and dry state and dissolved just prior to injection. This ability to store the wet and dry components separately within the device can increase the shelf life and thus increase the likelihood that the user will have an injector with effective dosages when an emergency arises.

In such devices it is required that the mixing and reconstitution processes are consistent and complete prior to injection.

SUMMARY OF THE INVENTION

It has been recognized that if a drug can be kept out of the liquid phase and stored as a dry medication, the shelf-life can be substantially increased and temperature susceptibility can be decreased substantially, thus allowing the efficacy and potency of the drug to endure longer and through harsher environments.

It has been recognized that a smaller drug delivery device than a conventional epinephrine auto-injector, which could be attached to a key chain and/or easily fit in a person's pocket, would make the device easier to carry and more likely that the user will have it on their person when needed. Various structures are contemplated herein which address many of the problems discussed above through the use of mixing structures, and actuation devices which ensure proper storage integrity, and full mixing prior to injection.

In particular, the embodiments contemplated herein include a mixing and injector device which can include a housing having a plurality of separate and distinct chambers disposed therein. Each of the plurality of chambers can include an associated displacement mechanism configured to reduce its respective effective volume. At least one of these chambers can be provided with a needle assembly which is configured to inject a mixed drug as provided by the device into an injection site. The needle assembly can further include a septum; a needle being separated from the plurality of chambers by the septum, the needle having a proximal end configured to pierce the septum in an actuated state; and a needle carrier, the needle carrier being configured to translate axially with respect to and toward the septum and the plurality of chambers thus enabling the needle to pierce the septum and provide fluid communication from the plurality of chambers through the needle in the actuated state.

It will be appreciated that the mixing and injector device can also include an actuation mechanism having a pre-loaded energy source, the pre-loaded energy source being configured to selectively cause the needle to pierce the septum and displace a fluid disposed in the plurality of chambers.

In various embodiments the mixing and injector device can include a sterility barrier disposed over a portion of the needle which can either be pierced or removed completely prior to or during an injection step In yet additional embodiments the mixing and injector device can also include a needle shield, the needle shield forming part of the actuation mechanism wherein the needle shield operates as a bump trigger, the needle shield being operatively connected to the actuation mechanism such that upon depressing the needle shield against an injection site a portion of energy is discharged from the pre-loaded energy source which pushes the needle carrier toward the injection site and to abut against the needle shield, the discharged energy also causing the septum to drive against the proximal end of the needle thus causing the needle to penetrate the septum and allow displacement of the fluid contained within the plurality of chambers through the needle.

In some embodiments the needle carrier can include an engagement flange, and wherein at least one of the plurality of chambers includes a septum protrusion housing the septum, the septum protrusion including a corresponding engagement flange, wherein the engagement flange of the needle carrier allows axial translation of the needle carrier along a length of the septum protrusion. In some such embodiments the engagement flange of the needle carrier can be provided as a radially inwardly protruding lip from an interior circumference of the needle carrier, and wherein the corresponding engagement flange of the septum protrusion is provided as a radially outwardly protruding lip from an exterior circumference of the septum protrusion.

In yet additional embodiments, a proximal end of the needle can be configured to be embedded within the septum in an initial or a stowed state.

In yet additional embodiments the needle carrier can be cylindrical in shape, wherein the septum protrusion is also cylindrical in shape. In some such embodiments the septum protrusion can then be configured to nest within the needle carrier.

In yet additional embodiments the plurality of separate and distinct chambers can include a first chamber and a second chamber, wherein the septum protrusion is provided about the second chamber, wherein the first chamber initially stores a liquid when the mixing and injector device is in a first stowed state, the second chamber initially storing a dry medicament when the mixing and injector device is in the first stowed state, the actuation mechanism configured to selectively displace the liquid from the first chamber into the second chamber.

These aspects of the invention are not meant to be exclusive and other features, aspects, and advantages of the present invention will be readily apparent to those of ordinary skill in the art when read in conjunction with the following description, appended claims, and accompanying drawings. Further, it will be appreciated that any of the various features, structures, steps, or other aspects discussed herein are for purposes of illustration only, any of which can be applied in any combination with any such features as discussed in alternative embodiments, as appropriate.

BRIEF DESCRIPTION OF THE DRAWINGS

The foregoing and other objects, features, and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention, wherein:

FIGS. 2A-B illustrate perspective exploded views of the medication mixing and delivery device and a mixing subassembly in accordance with the embodiment of FIGS. 1 A-C;

FIGS. 3A-D illustrate side cross sectional views of a medication mixing and delivery device through various actuation steps in accordance with the embodiment of FIGS. 1 A-C;

FIGS. 4A-D illustrate side cross sectional views of the mixing subassembly through various actuation steps for use in conjunction within the embodiment of FIGS. 1 A-C;

FIGS. 6A-E illustrate various exterior perspective views and cross sectional views of the enlarged area of the mixing subassembly as indicated by area A in FIG. 5E;

FIGS. 8A-E illustrate various exterior perspective views of the mixing subassembly and a secondary actuation mechanism through various actuation steps moving from the mixed state to an injected state as would be effectuated using the embodiment of FIGS. 1 A-C;

FIGS. 9A-B illustrate various exterior perspective views of a needle guard and associated subassembly through various actuation steps to shield an exposed needle after injection using the embodiment of FIGS. 1 A-C;

FIGS. 11A-E illustrate side cross-sectional views of a first embodiment of an auto injector through various states of actuation, the auto injector utilizing the septum and needle assembly of FIGS. 10A-B.

DETAILED DESCRIPTION OF THE INVENTION

It will be appreciated by those having skill in the area of fabrication and storage of drugs, that the lifespan and effectiveness of the drug can be increased substantially by keeping the medication in a dry state. Storage in a dry state also decreases the rate of degeneration as well as the degenerative effects of temperature, for example heat exposure. By keeping the drug in a dry state the breadth of environments where the device can be stored is increased while decreasing the frequency of required replacement.

The present invention illustrates various principles and devices which allow for the storage of a device having two or more components contained therein but which can quickly and reliably reconstitute, dissolve, fluidize, and/or put into a suspension, the components, i.e. mix them, immediately prior to delivery.

As such a system and method for storing and/or mixing a dry medicament component with a wet component for delivery to a user is contemplated herein. The system can include an auto-injector having various chambers therein, wherein the components of the drug are stored separately within the various chambers in various states so as to increase longevity, i.e. a dry drug component in one chamber, and a liquid, such as a solvent, in another. When the auto-injector is needed, the system can be actuated so as to mix the components, thus reconstituting, dissolving, fluidizing, and/or suspending a deliverable mixed drug, wherein the mixed drug can then be properly delivered to a patient. Examples of delivery can include, but are not limited to nebulization for inhalation, injection through a needle or cannula, topical application, etc.

With reference to FIGS. 1-9, shown is an exemplary embodiment of an auto-injector 10 in accordance with a first embodiment. The auto-injector 10 illustrates various aspects of the present invention, each of which will be discussed in more detail below.

Figure 1C:
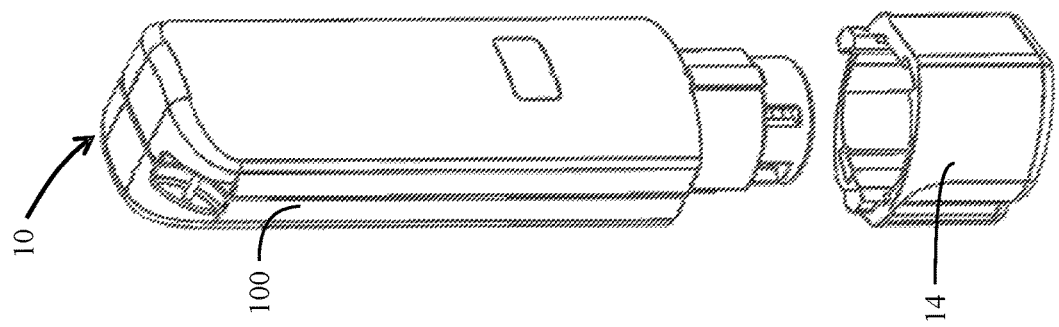
FIGS. 1A-C illustrate perspective exterior views of a medication mixing and delivery device through various actuation steps.
Figure 1B:
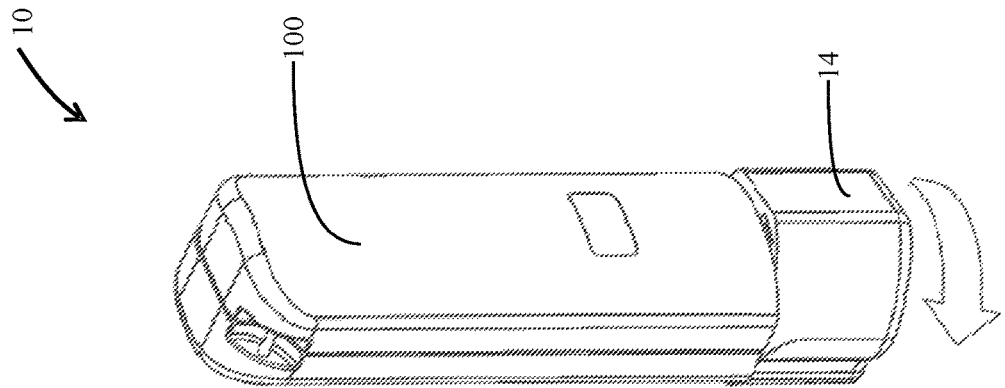
Figure 1A:
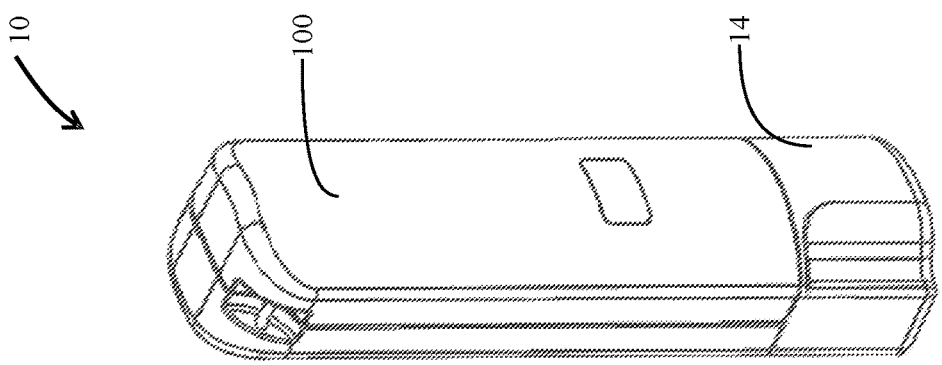

Referring to FIGS. 1A-C illustrate perspective views of an auto-injector which illustrates various aspects of the present invention. This embodiment illustrates an auto-injector 10 which has a housing 100 and a cap 14. The cap 14 can be in mechanical communication with a first actuation mechanism contained within the housing 100. By applying an axial torsional force between the cap 14 and the exterior housing, the actuator can cause certain components contained within the housing to initiate certain steps in the mixing process, for example open a valve between the various chambers, and move fluid contained in one chamber into the chamber containing the dry component of the medicament, which steps will be discussed in more detail below.

In certain embodiments, the cap 14 can be configured such that separation of the cap 14 from the housing 100 can be delayed until the device has moved completely from a stowed state to a completely mixed state. In this manner it can be ensured that the needle end of the auto-injector 10 is not exposed until the device is completely ready for delivery. Such mechanisms can include a threaded interface between the cap 14 and the housing 100, or the components can be keyed such that separation is not possible until a certain degree of rotation has been achieved, etc. Once the cap is removed, the injection end of the housing can then be exposed and a second actuation device triggered so as to inject or otherwise deliver the mixed medicament to a delivery or injection site, for example by depressing the housing up against the delivery site.

In other embodiments, the delivery of the mixed medicament to the injection site can be configured in such a way that the second actuation step cannot be activated until the device has moved completely from a stowed state to a completely mixed state. In this manner it can be ensured that the needle end of the auto-injector 10, while exposed after removal of cap 14, cannot be activated until the device is ready. Such embodiments are enabled by features internal to the device, which will be described below. Once mixing is complete, a second actuation device can be triggered so as to inject or otherwise deliver the mixed medicament to a delivery or injection site, for example by depressing the housing up against the delivery site.

FIGS. 2A-B illustrate an exploded view of an auto-injector 10 in accordance with one embodiment of the present invention. This exploded view illustrates the various internal components within the housing 100 and the cap 14. The housing can include a pre-loaded energy source 122 which is shown here as a spring, or which can be embodied as a compressed air chamber, which is not shown but could be adapted by those having skill in the art. The spring can be configured to provide a driving force and counter force between an inner plunger shaft 212, and transferred to various components of a mixing assembly 200 through various stages, as will be discussed below. The mixing assembly 200 can be contained within a frame 110 wherein individual components of the mixing assembly 200 can be configured to selectively rotate within the housing 100.

The mixing assembly 200 can be retained within the frame using a frame cap 114 which can be formed separately or unitarily with the frame 110. The frame cap 114 prevents the mixing assembly 200 from pushing through the frame 110 and exiting the housing 100 completely upon injection.

A needle shield 150 and needle shield spring 154 can be provide between the frame 110 and the housing 100 at an injection end of the housing 100. The needle shield spring 154 can be configured to bias the needle shield 150 axially downward so as to continuously restrict inappropriate exposure of the needle 310 prior to, during, and after injection.

The frame 110 and portions of the mixing assembly 200 can be configured to rotate together within the housing when an axially torsional force is applied between the cap 14 and the housing 100. The cap 14 can thus be coupled in a radially fixed manner to the frame 110 which is in turn coupled to certain components of the mixing assembly 200, and a driver interface 118 can also be provided which is rigidly coupled to the housing 100 as well as coupled in a radially fixed manner to alternative portions of the mixing assembly 200 such as to the inner plunger shaft 212. In this manner the axially torsional force and counter force applied between the cap and the housing can be transferred into and caused to actuate certain components of the mixing assembly 200.

The mixing assembly can include an inner plunger shaft 212 and an inner plunger 214 which together form a first displacement mechanism. The first displacement mechanism can be configured to reduce the effective volume of the first chamber, which will initially contain the wet solvent or other liquid component of the medicament.

The plunger 214 is configured to interface with an inner vial 210 which forms the first chamber. The inner vial can be housed within a vial sleeve 220, or alternatively the vial sleeve 220 and the inner vial 210 can be formed unitarily of a single material.

The vial sleeve 220 can then interface with a rotational valve seal 230 which sits within an intermediate support 240. The intermediate support 240 can have a second displacement mechanism 250, i.e. a second plunger, which is coupled thereto, the second plunger being configured to reduce the effective volume of a second chamber located within a second vial 270.

The second vial 270 can then be provided with a delivery assembly 300 affixed thereto which can include a needle 310 or cannula as well as a needle guard 314 or other barrier configured to maintain sterility of the delivery assembly prior to use.

FIGS. 3A-D and 4A-D illustrate cross sectional views of the auto-injector 10 and the mixing assembly 200 through various stages of mixing and delivery from a stowed state to a delivered state.

FIGS. 3A and 4A specifically illustrate a stowed configuration of the auto-injector 10 and the mixing assembly 200 contained therein. In this state the inner plunger shaft 212 is configured to rest on an upper edge of the inner frame 110 wherein the upper edge of the frame 110 is configured to prevent the pre-loaded energy source from releasing the energy stored therein and causing the plunger shaft 212 to depress and force the inner plunger 214 to move downward and reduce the effective volume of the interior of the inner vial, i.e. first chamber. Fluid communication between the first chamber and the second chamber, which is contained within the second vial 270, has not yet been established because an outlet of the inner or first vial (not shown here) is not aligned with the fluidic channel 254.

Dry medication can be kept in a recess 258 formed about an inlet of the second chamber within the second vial 270, such that fluid passing through the fluidic channel passes through or at least in close proximity to the dry medicament stored therein. It will be appreciated that the dry medication can also be stored in the fluidic channel connecting the first and second chambers, or merely kept in any portion of the second chamber wherein a specific recess is not provided.

In this stowed state the second chamber has its effective volume initially reduced to near zero by the second displacement device or plunger 250 so as to further decrease the space occupied by the auto-injector device 10, which decreased space occupation aides in allowing the device to be incrementally smaller, and thus easier to carry.

In this state the needle 310 and assembly, or other deliver mechanism, is retracted so as to prevent premature injection. The needle 310 is also still within the needle guard 314 so as to preserve sterility until the auto-injector is ready for injection.

It will be appreciated that the cap is not shown in these views for purposes of simplicity, however, the cap can, and will usually be, on for the stowed state.

FIGS. 3B and 4B illustrate a second intermediate state wherein the rotary valve is open and fluid communication is established between the first and second chambers just prior to depressing the plunger shaft 212 and the plunger 214. In this state a rotational force has been applied between the outer housing 100 which retains the driver interface 118 plunger shaft 212, vial sleeve 220, inner vial 210 and the valve seal 230 stationary with respect to the housing, then the counter force which is applied to the cap 14 can then be applied so as to twist the frame 110, and the intermediate support 240 which carries the fluidic channel. This opposing respective rotation between the plunger shaft 212, inner vial 210, and the rotational valve seal 230 causes two things to occur simultaneously: First, an outlet of the inner vial is caused to align with an inlet to the fluidic channel thus establishing fluidic communication between the inner vial 210 and the second chamber 270; second, a set of protrusions 216 off the plunger shaft 212 are brought into an axially aligned channel provided in the frame 110 which allows the plunger shaft 212 to be partially driven downward and cause displacement of the fluid contained in the inner vial through the fluidic channel and into the second vial or chamber 270.

In this embodiment, the respective rotation causes the outlet 224 of the first chamber or inner vial 210 which outlet is formed in the rotational valve seal 230 rotate about a central axis until it is aligned with the inlet fluidic channel 254. In some embodiments the rotational valve seal 230 can be configured to form the bottom wall of the inner vial 210, or the inner vial 210 and rotational valve seal 230 can be formed separately and distinctly.

As seen in FIG. 2, the rotational valve seal 230 of this embodiment is keyed having protrusions and channels or apertures corresponding to protrusions and apertures in the vial sleeve such that it remains stationary with respect to the vial sleeve and does not rotate as the cap and intermediate support 240 are rotated so as to allow selective alignment and misalignment between the outlet 224 and the fluidic channel 254. Alternatively, in embodiments being devoid a specific fluidic channel, alignment between the outlet 224 and an inlet of the second chamber can be required directly from the outlet 224 to the inlet of the second chamber so as to selectively allow or prohibit direct fluid communication therebetween.

In this state the second chamber still has its effective volume near zero by the second displacement device or plunger 250. Additionally, in this state the needle 310 or other deliver mechanism and assembly is still retracted so as to prevent premature injection as mixing has not yet occurred. The needle 310 is also still within the needle guard 314 so as to preserve sterility until the auto-injector is ready for injection and the needle shield 150 is still extended to prevent premature injection.

FIGS. 3C and 4C illustrate a mixed state wherein the intermediate support 240 and frame 110 have been rotated with respect to the mixing assembly 200 such that plunger protrusions 216 of the plunger shaft 212 have been aligned with an axially aligned channel of the of the vial sleeve 220 as well as through a channel in a sidewall of the intermediate support 240.

The axial alignment between the plunger shaft protrusions 216 and the channels allows axial translation of the plunger shaft 212 into the inner vial 210. Once this alignment has been achieved, the plunger shaft 212 is allowed to translate axially downward thus depressing the inner plunger 214 into the inner vial 210 which acts to displace the fluid contained therein through the outlet 224 through the fluidic channel 254 and into the second chamber contained within the second vial 270. The second vial 270 is permitted to expand its effective volume by being free to translate downward slightly within the frame and housing. As the second chamber expands to receive the fluid being displaced from the first chamber, the fluid passes through or into the recess 258, which contains the dry medicament, the fluid dissolves the dry component and mixes with the fluid as it enters the second chamber. In another embodiment, the fluid passes into the second chamber 270, without a recess 258, and with the powder being located elsewhere in the second chamber 270. The expanding volume of the second chamber still allows for sufficient mixing with the dry medicament to achieve appropriate mixing.

In the embodiment shown the intermediate support 240 includes similar protrusions resting on an intermediate stop 134 of the frame 110, and the plunger protrusions of the plunger shaft come to rest on the bottom of the intermediate support channel 130 on the intermediate stop 134 which indicates full depression of the first plunger 214 into the inner vial, which also signifies that mixing is complete and that the device is ready for the injection step.

In this state the needle 310 or other deliver mechanism and assembly is still retracted so as to prevent premature injection as mixing has not yet occurred. The needle 310 is also still within the needle guard 314 so as to preserve sterility until the auto-injector is ready for injection and the needle shield 150 is still extended to prevent premature injection. However, the needle shield 150, which forms part of a second trigger, is ready to be depressed and thus trigger injection. The functionality of the needle shield 150 will be discussed in greater detail below.

Figure 7D:
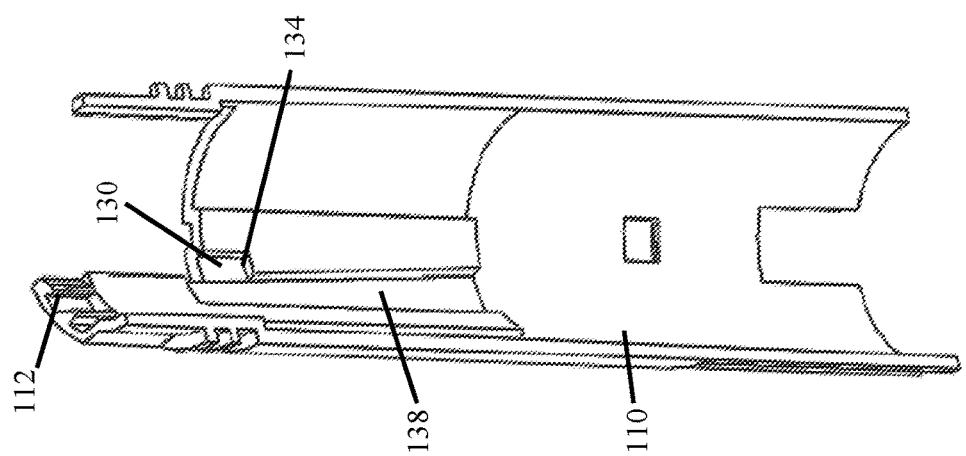
FIGS. 7A-D illustrate various perspective and cross sectional views of a frame being used within the medication mixing and delivery device of FIGS. 1A-C.
Figure 7B:
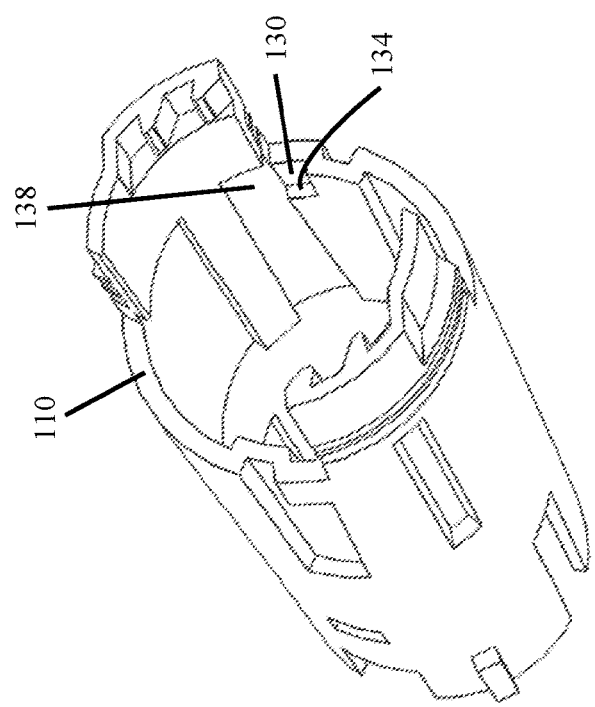
Figure 7C:
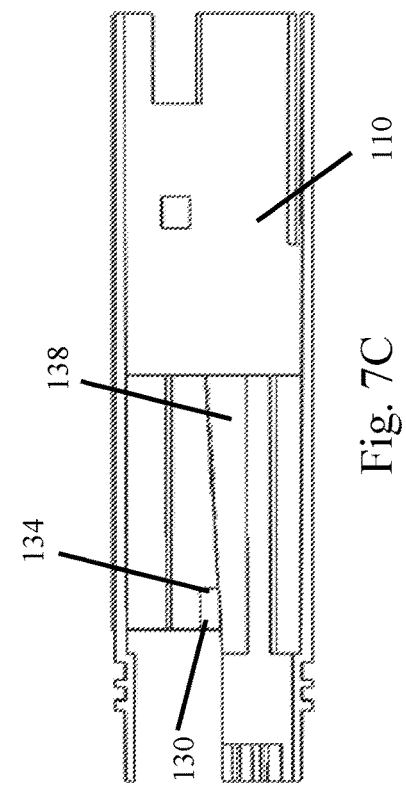
Figure 7A:
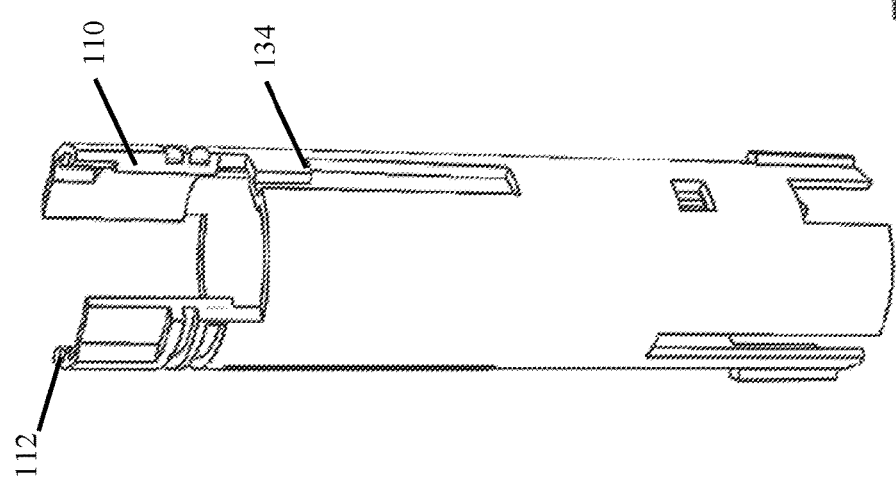

FIGS. 3D and 4D illustrate an injected state wherein the mixing assembly 200 has been rotated another small increment within the housing 100 of the auto-injector 10 such that protrusions of the plunger shaft 212 as well as additional protrusions, lower intermediate support protrusions 244 as seen in FIGS. 8A-E which will be discussed in more detail below, which are provided on the intermediate support 240 have been rotated around sufficiently so as to align with a second axially aligned channel, 138 as seen in FIGS. 7B-D, of the frame 110.

Once this alignment has been achieved, a second portion of energy stored within the pre-stored energy source which causes the entire mixing assembly to be pushed downward such that the needle guard 314 comes into contact with the frame cap 114 to stop the needle guard 314 such that the needle 310 punctures needle guard 314 and is extended through the needle guard 314. The needle 310 then extends further past the needle shield 150, and the needle 310 is thus extended into or about a delivery site, further as the second vial or chamber 270 hits the bottom portion of the frame cap 114, the second plunger 250 is depressed into the second vial or chamber 270 reducing its effective volume and causes the fluid to be ejected through the delivery assembly and into the patient or onto the delivery site.

FIGS. 5A-E illustrate perspective views of the mixing assembly 200 within the frame 110 which illustrate various stages of actuation through the mixing and injection process.

Figure 5A:
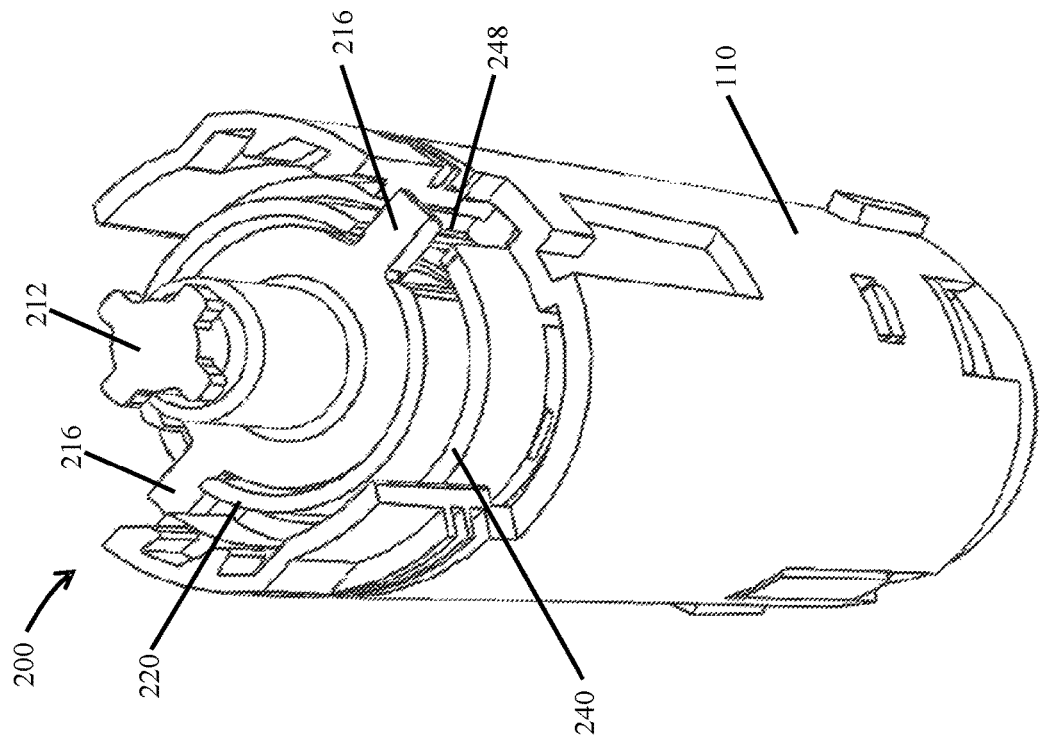
FIGS. 5A-E illustrate various exterior perspective views of the mixing subassembly, within the frame, through various actuation steps moving from a stowed state to a mixed state as would be effectuated using the embodiment of FIGS. 1 A-C.

In particular, FIG. 5A illustrates the relative position of the mixing assembly 200 with respect to the frame 110 in a stowed state. In this state the plunger shaft 212 is provided with a plurality of plunger protrusions 216 which extend radially outward and rest on an upper lip of the intermediate support 240. It will be appreciated that the vial sleeve 220 is also provided with a channel through which the plunger protrusions 216 extend and allow for axial translation in later steps of actuation. In this manner the plunger shaft is maintained in a non-depressed or stowed state wherein rotation of the plunger protrusions 216 into the middle support channel 248 must be effectuated before the plunger shaft 212 can translate axially and depress into the vial (not shown) contained within the vial sleeve 220.

Figure 5B:
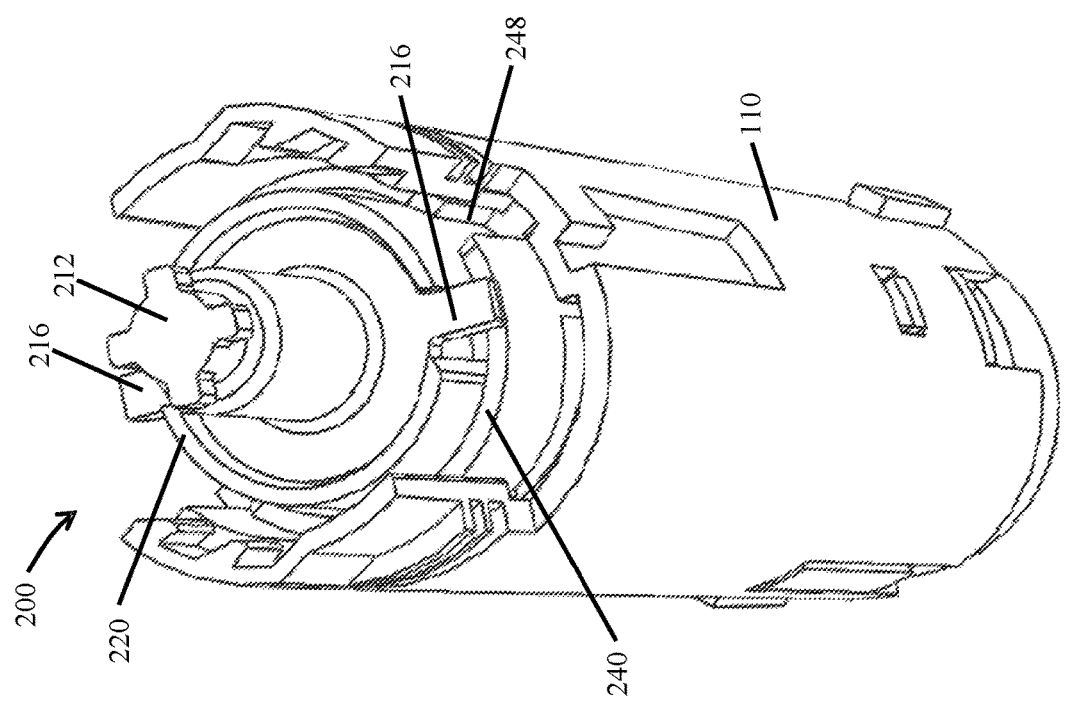
Figure 5D:
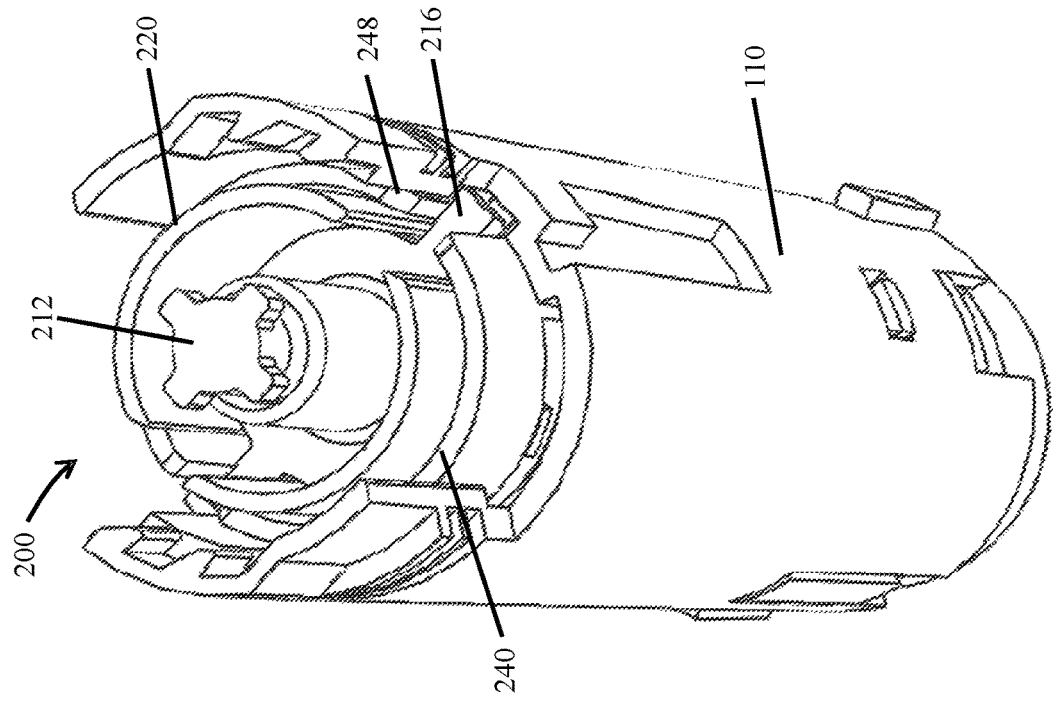
Figure 5C:
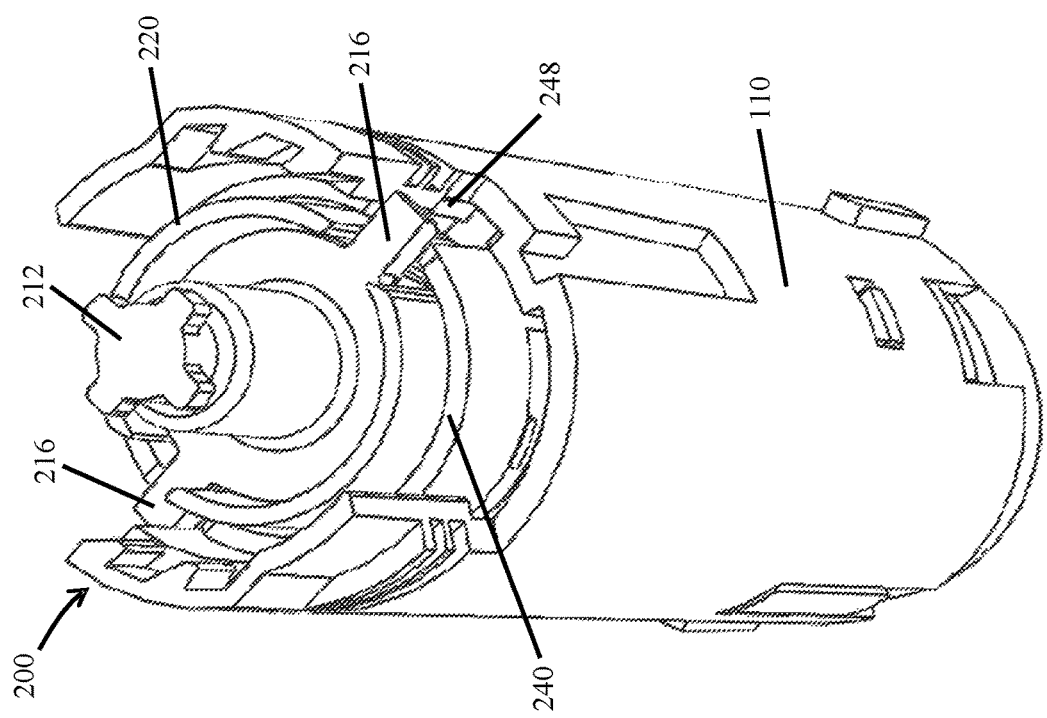

FIGS. 5B-D illustrate the travel of the rotated state of the plunger shaft 212 with respect to the vial sleeve 220 and intermediate support 240. The plunger protrusions 216 are aligned with the channel 248 and are thus ready for release of a portion of energy contained in the pre-loaded energy source to depress the plunger shaft 212 into the vial sleeve 220 and the vial contained therein (not shown) so as to displace the fluid contained therein. In this embodiment, the rotation of the plunger shaft also causes rotation of the vial sleeve 220, which rotation causes the outlet of the first chamber to align with the inlet of the fluidic channel leading to the second chamber. In this manner, the alignment, and thus opening of the fluidic channel, occurs simultaneously with the alignment of the protrusions 216 with the intermediate support channel and allows the pre-loaded energy source to depress the plunger shaft 212.

FIG. 5C illustrates an intermediate partially depressed state and FIG. 5D illustrates a mixed configuration wherein the plunger shaft and plunger have been fully depressed into the first chamber displacing all of the liquid into the second chamber.

Figure 5E:
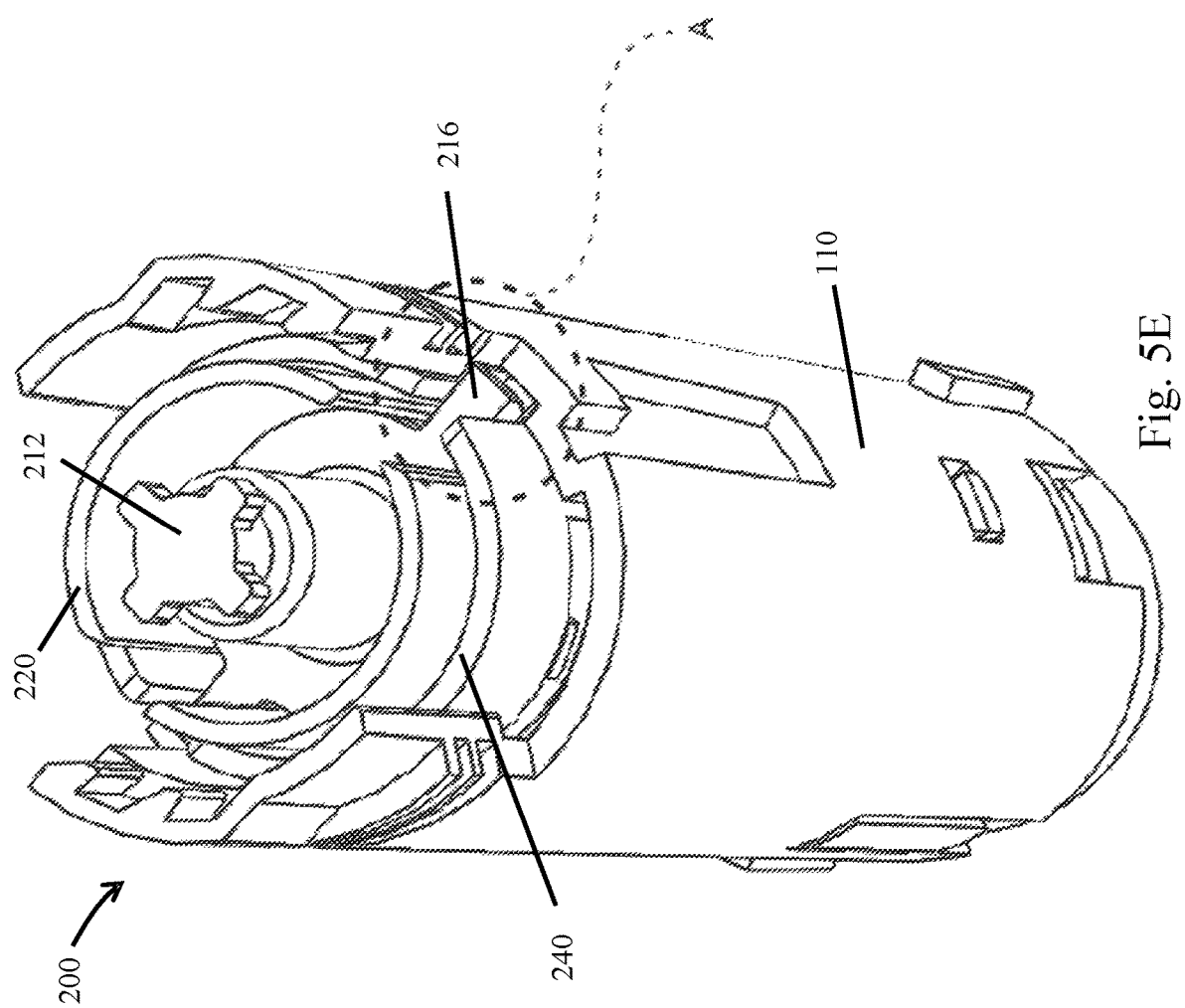

FIG. 5E illustrates a fully mixed state wherein the auto-injector is fully ready for injection. The area A as illustrated in FIG. 5E will be discussed in further detail wherein the mixing assembly 200, which includes the intermediate support 240 together with the vial sleeve 220 and plunger shaft 212 all need to rotate a small distance into the frame 110 so as to initiate the injection step.

FIGS. 6A-E illustrate various perspective detailed and cross sectional views of the area A as defined in FIG. 5E. As discussed above the frame is provided with a plurality of channels. The first frame channel 130 and the intermediate stop 134 have a pair of upper support protrusions 242 of the intermediate support supported therein. After the mixing stage is complete the protrusions 216 of the plunger shaft 212 are resting on the intermediate support 240 on top of the upper support protrusions 242.

In order to translate axially downward to eject the fluid through the delivery assembly the intermediate support 240, vial sleeve 230 and the inner plunger must rotate together so as to be aligned with a second frame channel so as to allow for a second portion of energy to be released from the pre-loaded energy source thus driving the mixing assembly downward, with the delivery assembly affixed to the bottom end thus effectuation injection or delivery. To move from the mixed state and begin injection the upper support protrusions 242 along with the plunger shaft protrusions 216 are rotated radially into a second frame channel 138 as seen best between the positions illustrated in FIG. 6D to FIG. 6E.

In particular, FIGS. 6A-B illustrate perspective exterior and cross sectional views of the interface shown by area A of FIG. 5E wherein the auto injector and mixing assembly is in a mixed state with the plunger protrusions 216 being depressed against the intermediate support 240 and associated upper support protrusions 242. All of which rests on the intermediate stop 134 within the first frame channel 130.

FIGS. 6C-D illustrate perspective exterior views of the interface shown by area A of FIG. 5E wherein the auto injector and mixing assembly is in a mixed state but more importantly illustrating an intermediate rotation of the plunger and upper support protrusions 216 and 242 respectively with respect to the frame 110 into an aligned configuration with the second frame channel 138 just prior to injection.

Figure 6E:
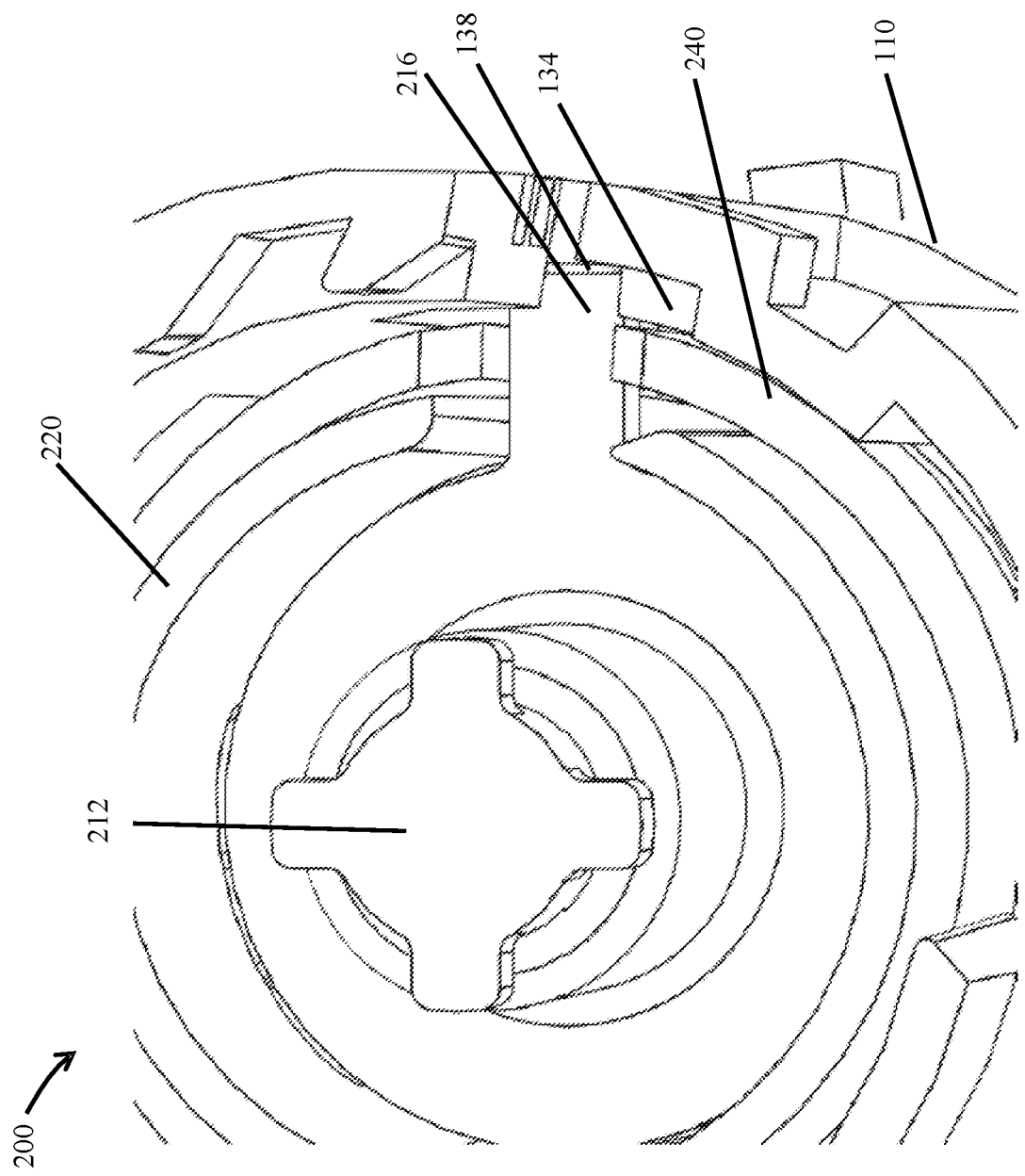

FIG. 6E illustrates the mixing assembly 200 as it is being further depressed into the frame 110 wherein the plunger shaft 212 and protrusions 216 along with the intermediate support 240 are depressed downward thus driving the delivery assembly (not shown) downward to inject the needle, until the second vial engages the lower end of the frame, stops, and the intermediate support (not shown) then drives the second plunger (not shown) into the second vial displacing the mixed drug out of the delivery assembly and into the delivery site. It is this reason, as described above, that the second actuation, which results in the translation of the mixing assembly downward, will not occur until mixing is complete. The plunger protrusions 216 will not rotate with the upper support protrusions 242 until they are able to rotate together, clear the frame and access the second frame channel 138. If the user attempts to actuate the second actuation mechanism prior to plunger protrusions 216 coming into contact with upper support protrusions 242, the mixing assembly will get stopped from entering the second frame channel 138 by the frame 110. This mechanism is helpful in preventing the second actuation step from occurring until all of the fluid from the first chamber has been transferred into the second chamber.

FIGS. 7A-D illustrate various perspective exterior and cross sectional views of the frame 110. These views illustrate the interior first frame channel 130 and second frame channel 138 with more clarity. These views also illustrate the intermediate stop 134 upon which the upper support protrusions of the intermediate support rests (not shown). In some embodiments the second frame channel 138 can have a tapered channel when effectively increases the width of the second frame channel 138 as the various protrusions travel downward within the second frame channel 138. This tapering ensures that the various protrusions do not bind up during the injections step, and allow the protrusions to travel freely downward until the second vial hits the stops, signaling full needle extension and driving of the second plunger into the vial thus fully ejecting the mixed fluid and medication compound.

FIGS. 7A-D also illustrate a safety mechanism in the form of cap rotation locks 112 which interface with an upper portion of the plunger shaft as well as the driver interface such that once the cap is rotated a certain degree, a corresponding protrusion enters into and meshes with the teeth of the cap rotation lock 112 of the frame and prevents the cap from being twisted back. In this manner, if the cap is inadvertently twisted, and a risk of premature mixing is presented by such rotation, a user cannot simply twist the cap back and place the auto-injector back into storage believing that no mixing has occurred. It will be appreciated that, once mixed, even partially, the dry drug will typically begin to degrade at an increased rate. The purpose of the lock is to prevent accidental mixing, or at least signal to the user that the drugs inside might have been previously mixed, wherein instructions on whether or not to use in the case of premature mixing can be provided.

FIGS. 8A-E illustrate how the needle shield 150 can be configured in one embodiment to act as a bump switch and trigger the injection step by providing the slight rotation of the protrusions 216 and 242 off of the intermediate stop (not shown here) and into the second frame channel discussed above, (not shown). It will be appreciated that this view of the mixing assembly 200 and needle shield 150 are shown herein without the frame so as to better illustrate the interaction of the needle shield 150 with the mixing assembly 200. However, it will be appreciated that the slight rotation shown here provides the rotation as illustrated in FIGS. 6C-E.

In the embodiment shown in FIGS. 8A-E an upward force is applied to the needle shield 150 by depressing the injection end of the auto-injector against the delivery site. In response to this depression force, the needle shield 150 translates upward within the housing and frame such that a lower support protrusion 244 is released from a needle shield hook 158. The needle shield hook prevents premature rotation of the intermediate support off of the intermediate stop during the changing of states from the stowed state to the mixed state by rotation of the vial sleeve and inner plunger as discussed above, preventing the intermediate support from rotating with those components during mixing and thus preventing premature injection. Additionally, the shield hook 158 can be configured so as to transfer the axially rotational force to be applied to the cap, through the frame, and into the intermediate support, which allows for relative rotation between the rotational valve seal, as discussed above, and the fluidic channel disposed within the intermediate support so as to allow initial opening of the rotary valve.

Figure 8E:
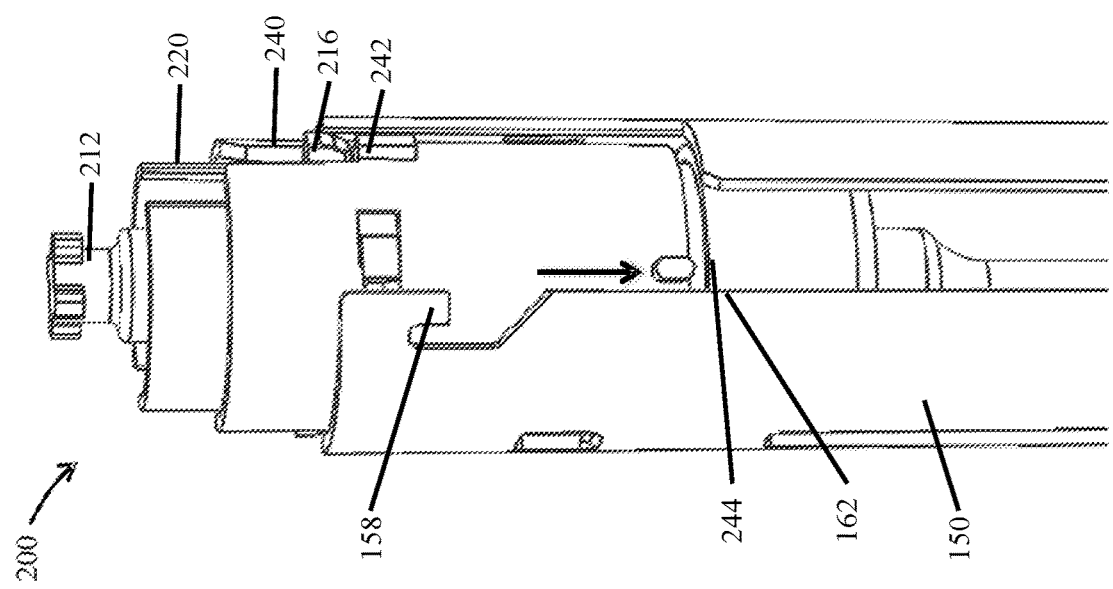
Figure 8D:
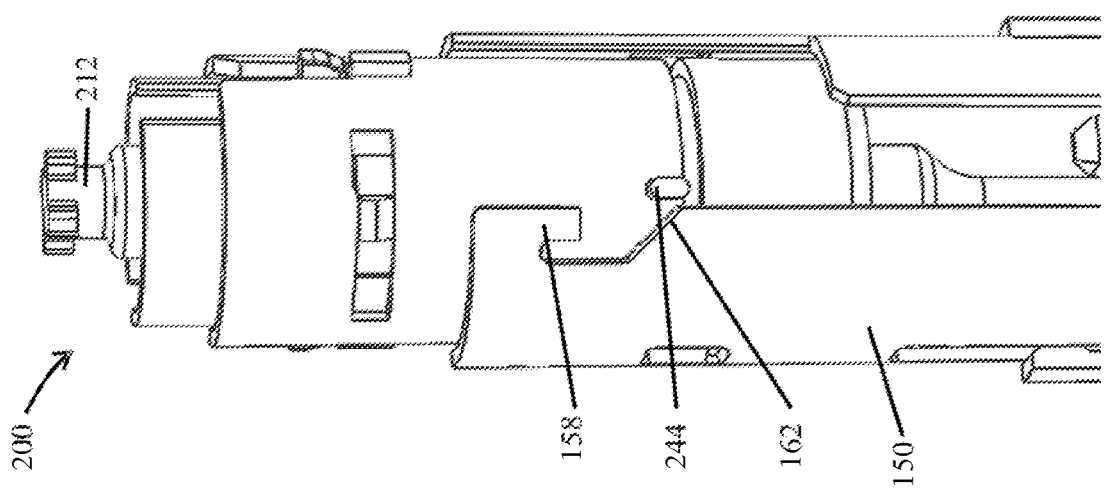

As the needle shield 150 translates upward, the lower support protrusions 244 of the intermediate support interface with a needle shield cam ramp 162. As the needle shield 150 continues to travel upward relative to the intermediate support, the lower support protrusions 244 slide on the needle shield cam ramps 162 and a rotation of the entire mixing assembly 200 is induced as shown in FIG. 8C. In this embodiment the width of the needle shield cam ramps 162 corresponds with a radial distance required to move the upper support protrusions 242 and the plunger protrusions 216 off of the intermediate stop and into the second frame channel which corresponds to the released configuration as illustrated in FIG. 8D. Whereupon, as shown by FIG. 8E the entire mixing assembly 200 can travel downward by force applied from the pre-stored energy source and result in injection or other delivery.

FIGS. 9A-B illustrate an extension and locking function of the needle shield 150. It will be understood that it is of general interest to reduce the potential for inadvertent contamination or sticks of other people prior to injection, during injection, and after injection. As such the needle shield 150 of the present embodiment serves both as a bump switch as well as a protective barrier between the user, and other people from inadvertent sticks, jabs, or cuts from an exposed needle. As such, after the bump switch is activated, the needle shield hook, as discussed above, is released and a needle shield spring 154, as shown in FIG. 2, or other biasing mechanism, is released so as to push the needle shield outward, or axially downward after activation. The delivery assembly and needle are not ejected until the bump switch is first activated, then after injection, as the user pulls the auto-injector away from the delivery site, the needle shield is simultaneously extended until it clears past the tip of the needle, essentially eliminating the risk of secondary pricks and cross contamination of bodily fluids to other people post injection.

In the embodiment shown the frame cap 114 can be provided with a plurality of protrusions, both lock protrusions 116 for interfacing with one or more needle shield guide channels 166 and needle shield extension lock tabs 170 which interface with the interior of the frame or housing. The guide channels can have space for allowing initial depression whereupon the extension lock protrusions can slide up and then interferingly engage with the lock tabs in a fully extended state after injection. The tabs can prevent pulling the needle shield 150 completely free from the housing as well as prevent a secondary depression of the needle shield 150 which would expose the extended needle.

Figure 10B:
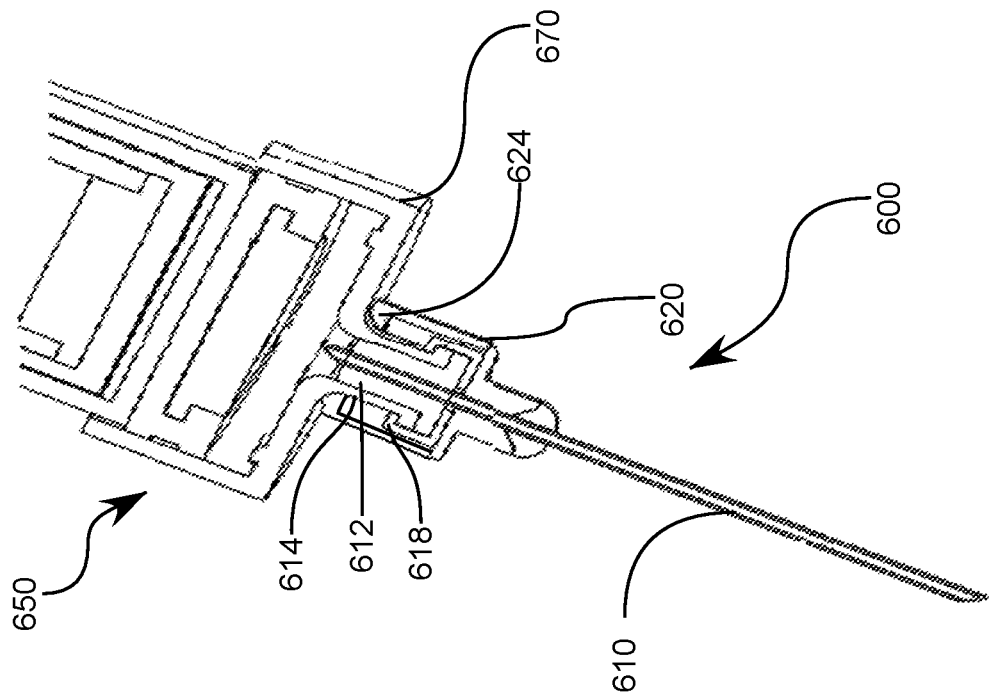
FIGS. 10A-B illustrate side cross-sectional views of extended and retracted states of a septum and needle assembly adaptable for use in the auto injectors the aforementioned embodiments.
Figure 10A:
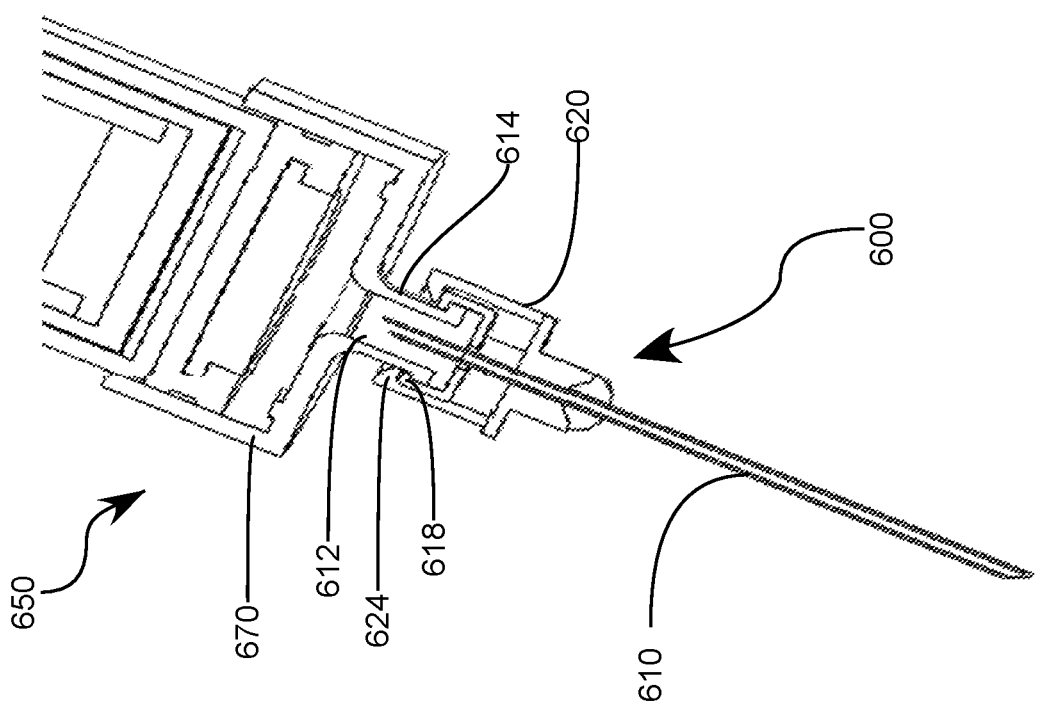

FIGS. 10A-B illustrate a adaptable for use with any of the auto-injectors discussed above. FIG. 10A illustrates an exemplary mixing assembly 650, similar to any of the mixing assemblies disclosed herein, the mixing assembly 650 having an expanded second chamber 670 containing the mixed drug and liquid component just prior to injection. A septum 612 is provided between the inlet end of the needle 610 and separates the interior channel or cannula of the needle from introducing contaminants therethrough into the second chamber 670 prior to injection. Additionally the septum 612 separates the needle 610 from the interior of the second chamber 670 so as to prevent premature leaking and full mixing of the various components prior to actuation and injection.

It will be appreciated that the needle 610 has both a distal or injection end and a proximal end. The distal end can be configured to enter into a patient at an injection site and the proximal or inlet end being configured to pierce and ultimately penetrate the septum. It will be further appreciated that in FIG. 10A the needle 610 has still not yet penetrated the septum 612.

As shown in FIG. 10A, the needle 610 can be partially embedded into, but not fully penetrated through, the septum 612 in a stowed state wherein the needle 610 can penetrate the septum 612 and open fluid communication out the injection end just prior to injection.

In order to provide penetration of the septum 612 by the needle 610, the needle can be carried by a translating needle carrier 620. The needle carrier 620 can have a translating body which is allowed to translate axially along the needle axis with respect to the second chamber 670 and the septum 612. The degree of translation can be limited or controlled by providing abutting shoulder protrusions, i.e. 618 and 614 respectively, which interfere with one another at certain points along the relative travel distance between the carrier and the second chamber. In one instance the shoulders can engage to prevent the needle from being released from the system and sliding out of the auto injector entirely, and in another instance the shoulders can engage to provide the axial translation and puncture force of the needle through the septum when pushed down just prior to injection. In the cross sectional view of FIG. 10A the needle carrier is extended to its maximum distance away from the second chamber.

FIG. 10B illustrates the injection motion of pressing the auto injector up to an injection site. The downward force drives the needle 610 downward with respect to the needle shield to expose the needle from the interior of the auto injector body. A shoulder or stop can be provided on the interior of the needle shield which engages with the needle carrier and pushes the proximal end of the needle through to fully penetrate through the septum. At this point a fluid pathway is established and fluid communication is provided from the second chamber into the patient's body or other injection site. Once fluid communication has been established a second plunger, i.e. displacement mechanism, can be pushed into the second chamber thus forcing the mixed drug into the injection site.

FIGS. 11A-E and FIGS. 12A-F illustrate two various embodiments of auto injectors 20 and 30 respectively which utilize the needle assembly 600 of FIGS. 10A-B.

These embodiments both include auto injectors having housings 500 which house mixing assemblies 200, which work identically to those discussed above with respect to FIGS. 2-8. It will be appreciated that the needle assemblies of the previously discussed embodiments have been changed so as to incorporate the septum 612 having the needle embedded therein as discussed with respect to FIGS. 10A-B.

As discussed above, the mixing assembly 200 can include one or more displacement mechanisms corresponding to each of the plurality of chambers disposed within the housing, which function as discussed above.

However, these embodiments also include a needle assembly 600 provided about a second chamber of the mixing assembly 200, the needle assembly 600 including a septum 612, and a needle 610. It will be appreciated that the needle 610 has a proximal end being embedded within the septum in a stowed state wherein the septum 612 separates the needle from the plurality of chambers until after actuation into an actuated state. As such FIG. 11A illustrates an unmixed and stowed state, and FIG. 11B illustrates the beginning of actuation wherein fluidic communication has been established with a second chamber. FIG. 11C illustrates a mixed state ready for actuation of the needle assembly and subsequent injection. In this state the needle 610 has still not penetrated the septum 612 fully. FIG. 11D illustrates downward motion of the mixing assembly 200 after injection has been triggered by pressing the needle guard 550 onto an injection site wherein the mixing assembly is driven downward, collapsing the sterility barrier 514 and sandwiching the needle assembly 600 between the needle guard 550 and the downward travelling mixing assembly 200. The needle assembly 600 is provided with a needle carrier 620, which is configured to translate axially along a septum protrusion 614, i.e. a neck portion having a volume extending from the second chamber or vial, which contains the septum 612. This axially translation caused by the sandwiching of the needle assembly 600 between the mixing assembly 200 and the needle guard 550 causes the needle carrier to drive the needle upward with respect to the mixing assembly 200 and pierce the septum 612 as illustrated in FIG. 11D. At this point the pre-loaded fluid communication has been established between the second chamber and the needle 610, thus allowing the energy source, i.e. the spring driving the mixing assembly 200 downward, to also cause the second displacement mechanism to displace the mixed drug from the second chamber, through the needle 610, and into the delivery or injection site as shown in FIG. 11E.

Figure 12A:
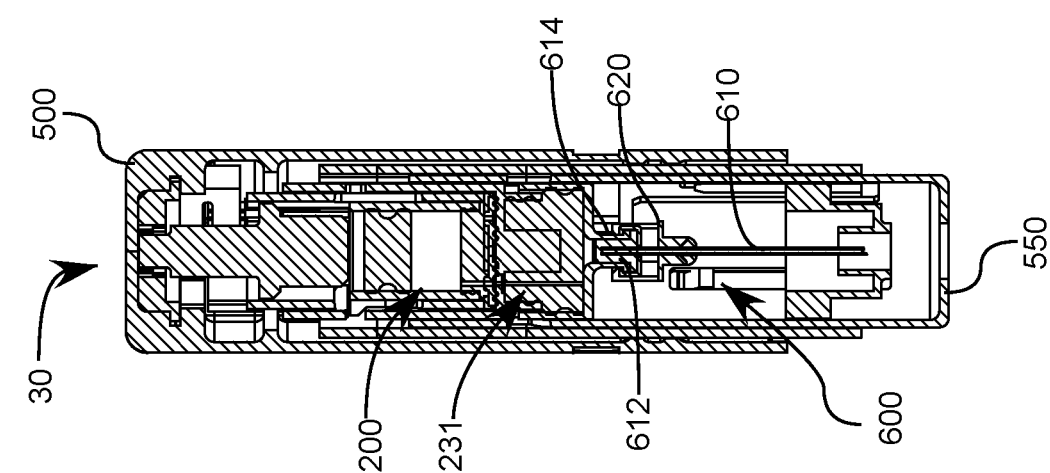
FIGS. 12A-F illustrate side cross-sectional views of an alternative embodiment of an auto injector through various states of actuation, the auto injector utilizing the septum and needle assembly of FIGS. 10A-B.
Figure 12B:
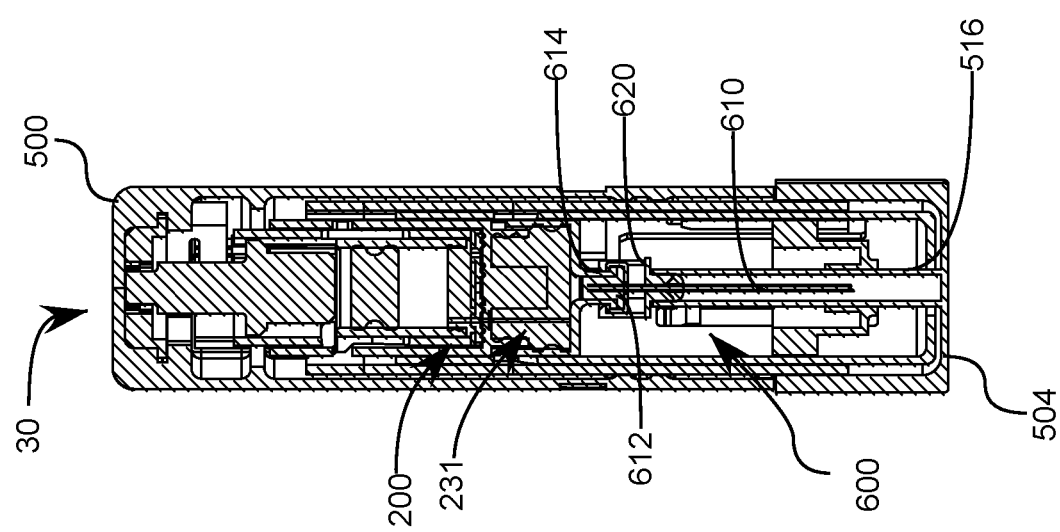
Figure 12C:
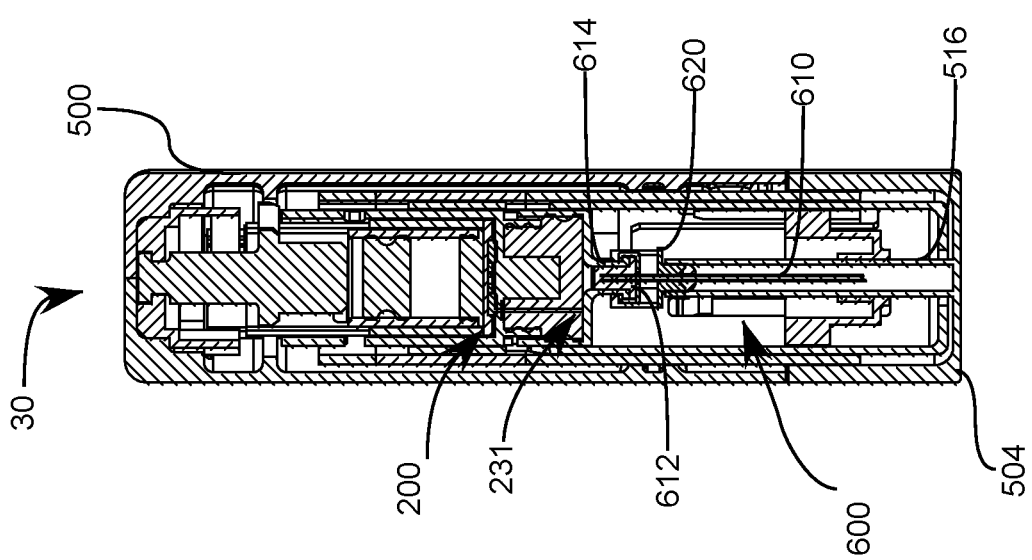
Figure 12F:
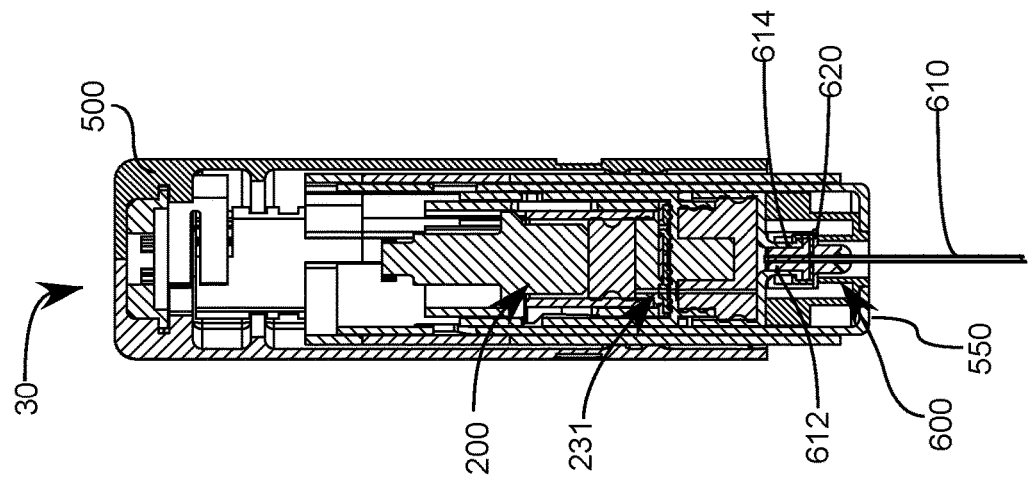
Figure 12E:
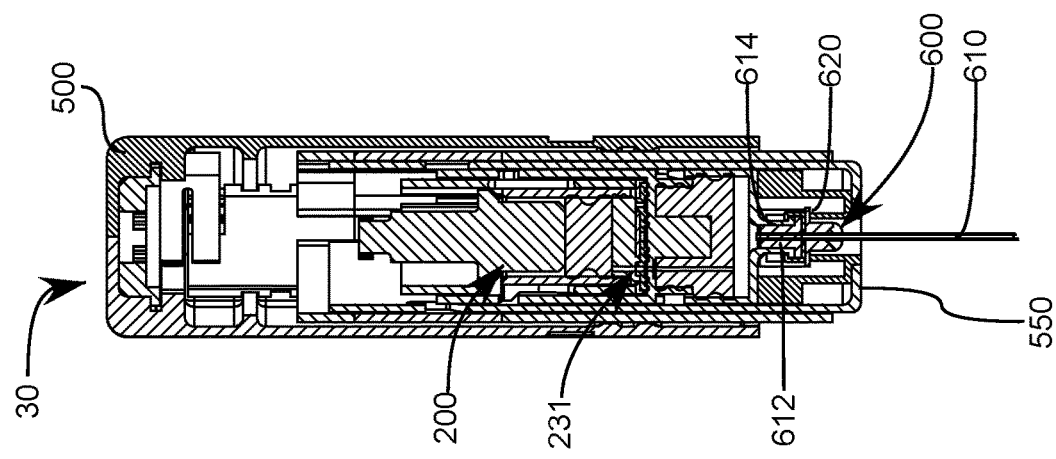
Figure 12D:
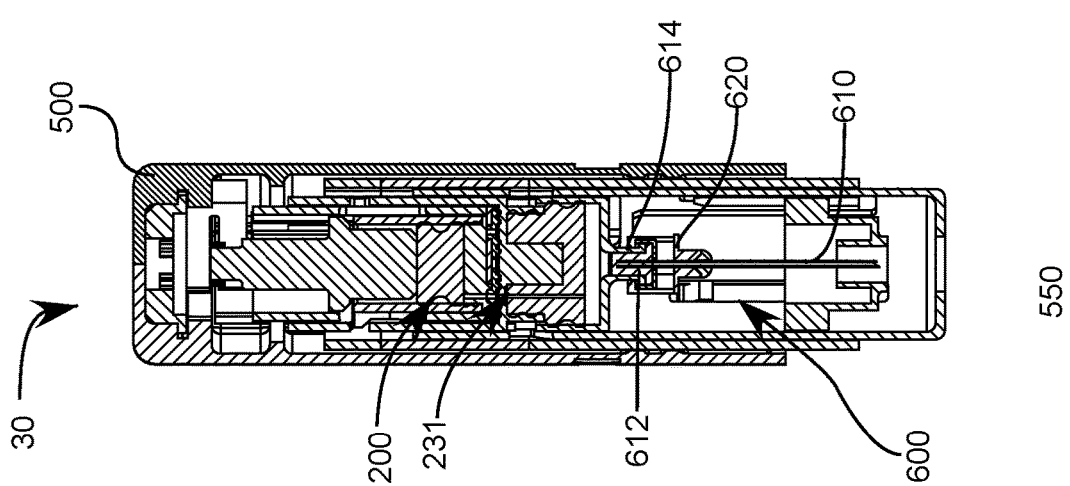

FIGS. 12A-F illustrate an auto injector 30 having a similar construction with regard to actuation and piercing of the septum of the auto injector 20, however in this embodiment instead utilizes a cap 504, and a sterility barrier 516 being affixed to the cap. In this embodiment mixing is actuated by the twisting of the cap, i.e. moving from the state shown in FIG. 12A which illustrates a fully stowed state to the position illustrated in FIG. 12 B showing the valve between the first and second chambers to be open. Once fully rotated, the cap 504 can be removed, and the sterility barrier 516 taken with it, as shown in FIG. 12C. The fluid can then be pushed from the first chamber to the second chamber using an actuation mechanism which releases some energy from the pre-loaded energy source, wherein the septum has still not been pierced, as shown in FIG. 12D. which causes fluidic communication between a first and a second chamber as shown in FIG. 12B. The actuation mechanism can then cause the mixing assembly 200 to be driven downward to come into contact with the needle shield 550 as shown in FIG. 12E thus sandwiching the needle assembly 600 and causing the septum 612 to be pierced, similar to the embodiment of FIGS. 11A-D, as well as causing the needle 610 to penetrate at the injection site. Again, this piercing allows for fluid communication of the second chamber through the needle 610 and into the injection site, but restricts fluid communication entirely until after the septum 612 is pierced.

It will be appreciated that the needle carrier 620 can be crimped around the septum protrusion 614 thus resulting in an engagement flange 624 that prevents the needle carrier from premature separation or pulling of the needle from the septum. In this manner proper embedding depth of the needle into the septum can be ensured. Additionally, the septum protrusion 614 can be provided with a corresponding engagement flange 618 which engages the engagement flange at a maximum extension length so as to ensure proper positioning. It will be appreciated that the septum protrusion and the needle carrier can correspond in shape, and while shown as cylindrical, can be provided in virtually any cross sectional shape.

It will also be appreciated that the septum 612 nests within the needle carrier, however, the needle carrier can also be configured so as to nest into an interior portion of the septum protrusion where the septum protrusion is crimped around the needle carrier, instead of vice versa.

In another embodiment, needle 610 does not need to be partially embedded in septum 612 prior to effectuating the injection. As such, the needle 610 can instead be maintained at some distance away from septum 612 whereby the septum 612 is pierced entirely upon the actuation of injection.

Also with particular reference to FIGS. 12A-F, and as discussed above, it is contemplated that the mixing assembly can be actuated and thus moved from a stowed state to a mixed state through a rotation and subsequent removal of a cap, such as the cap 504. In the embodiment shown in FIGS. 12A-B in particular, a sterility barrier 516 is shown which is affixed to the cap such that upon removal of the cap, the sterility barrier 516 is removed therewith. The sterility barrier 516 can be sealingly engaged through a press fit or otherwise bonded around the needle carrier 620 such that the sterility barriers attachment to the needle carrier 620 is broken when pulled, or otherwise placed in tension, prior to the breaking of a bonding or connection of the sterility barrier 516 to the cap 504. In this manner the sterility barrier can be completely removed so as to not interfere with the downward motion of the mixing assembly upon actuation of the injection trigger, i.e. compression upon injection. Removal of the sterility barrier allows for a smaller and/or less powerful spring, because the compression of the sterility barrier provides a counter-active or backwards force for the spring to overcome when it is not removed.

It has also been recognized that the tensile force required to pull the sterility barrier 516 from the needle carrier 620 is or can be transmitted to the second vial 270 of the mixing assembly 200 which tensile force can potentially be sufficient to pull the second vial 27 free of the second displacement mechanism or plunger instead of pull the sterility barrier 516 free. In such a case the internal displacement mechanism can get jammed, the mixed medication spilled, or any number of potentially unwanted effects. In order to prevent this premature separation, it has been recognized that various methods can be utilized to minimize or remove the risk around movement in the second vial 270 upon removing the sterility barrier. It will be appreciated that various filling methods which either remove air/gas by bypassing the various plungers, or alternatively the vials can be filled under vacuum conditions so as to improve the retention force, by providing an increased vacuum force within the mixing assembly 200.

The break-away force of the sterility barrier needs to be less than the retention or tensile-force required to maintain proper position of the lower vial. Alternatively, increasing the retention or tensile force to maintain proper position is also a sufficient method.

It has also been recognized that the septum 612 and the separation of the needle from the second vial 270 thereby, also allows the mixing assembly to remain in a sealed state until after the sterility barrier has been removed, and just prior to ejection of the mixed drug therethrough. It will be appreciated that because the needle does not pierce the septum 612 until after the sterility barrier has been removed, that the translation of the lower vial 270 in response to this tensile force will be mitigated as the tensile force will only increase the volume without allowing increase in material contained therein, and thus will only increase the vacuum pressure differential which vacuum pressure differential will tend to hold the lower or second vial 270 in place.

Other methods of increasing the vacuum or negative pressure differential include sealing or closing the valve 231 while lower vial 270 is under vacuum or after lyophilizing a dry medicament contained within the second vial 270, wherein lyophilization typically requires a vacuum for the drying of a medicament cake in a porous state. If, instead of backfilling with nitrogen, the vacuum or negative pressure is maintained, there is the benefit of the ability to better maintain the position of the lower vial 270 with respect to its displacement mechanism under the application of a tensile force, i.e. to remove the sterility barrier 516.

It will also be appreciated that similar stoppers or engagement lips can be provided between the second vial 270 and it's respective displacement mechanism so as to limit extension and potential separation. Such structures could allow for a press fit or interference fit, however, these embodiments are not shown herein, but are never-the-less contemplated as potential beneficial structures.

While the principles of the invention have been described herein, it is to be understood by those skilled in the art that this description is made only by way of example and not as a limitation as to the scope of the invention. Other embodiments which are not discussed herein but which constitute obvious variants are therefore contemplated herein and as such fall within the scope of the present invention in addition to the exemplary embodiments shown and described herein. It will be further appreciated that while the various embodiments have been discussed separately herein, that each of the embodiments can be modified so as to incorporate features or options of any of the alternative embodiments without departing from the inventive concept contained herein. Modifications and substitutions by one of ordinary skill in the art are thus considered to be within the scope of the present invention.

The invention claimed is:

1. A mixing and injector device comprising:
   a housing having a plurality of separate and distinct containers disposed therein;
   one or more displacement mechanisms corresponding to each of the plurality of containers disposed within the housing;
   a needle assembly being provided about one of the plurality of containers, the needle assembly further comprising:
      a septum;
      a needle being separated from the plurality of chambers by the septum, the needle having a proximal end configured to pierce the septum in an actuated state; and
      a needle carrier, the needle carrier being configured to translate axially with respect to and toward the septum and the plurality of chambers thus enabling the needle to pierce the septum and provide fluid communication from the plurality of chambers through the needle in the actuated state; and
   an actuation mechanism having a pre-loaded energy source, the pre-loaded energy source being configured to selectively cause the needle to pierce the septum and displace a fluid disposed in the plurality of containers.

2. The mixing and injector device of claim 1, further comprising a removable sterility barrier being affixed to the needle assembly, wherein a breakaway force required to remove the sterility barrier is less than a positional retention force of a second container to which the needle assembly is attached.

3. The mixing and injector device of claim 2, wherein the positional retention force includes a vacuum generated by the breakaway force.

4. The mixing and injector device of claim 1, further comprising:
   a needle shield, the needle shield forming part of the actuation mechanism;
   wherein the needle shield operates as a bump trigger, the needle shield being operatively connected to the actuation mechanism such that upon depressing the needle shield against an injection site a portion of energy is discharged from the pre-loaded energy source which pushes the needle carrier toward the injection site and to abut against the needle shield, the discharged energy also causing the septum to drive against the proximal end of the needle thus causing the needle to penetrate the septum and allow displacement of the fluid contained within the plurality of containers through the needle.

5. The mixing and injector device of claim 1, wherein the needle carrier includes an engagement flange, and wherein at least one of the plurality of containers includes a septum protrusion housing the septum, the septum protrusion including a corresponding engagement flange, wherein the engagement flange of the needle carrier allows axial translation of the needle carrier along a length of the septum protrusion.

6. The mixing and injector device of claim 4, wherein the needle carrier includes an engagement flange, and wherein at least one of the plurality of containers includes a septum protrusion housing the septum, the septum protrusion including a corresponding engagement flange, wherein the engagement flange of the needle carrier allows axial translation of the needle carrier along a length of the septum protrusion.

7. The mixing and injector device of claim 5, wherein the engagement flange of the needle carrier is provided radially inward from an interior circumference of the needle carrier, and wherein the corresponding engagement flange of the septum protrusion is provided radially outwardly from an exterior circumference of the septum protrusion.

8. The mixing and injector device of claim 5, wherein the needle carrier is cylindrical in shape, and wherein septum protrusion is cylindrical in shape and nests within the needle carrier.

9. The mixing and injector device of claim 1, wherein a proximal end of the needle is initially embedded within the septum in a stowed state.

10. The mixing and injector device of claim 6, wherein the plurality of separate and distinct chambers includes a first container and a second container, and wherein the septum protrusion is provided about the second container, wherein the first container initially stores a liquid when the mixing and injector device is in a first stowed state, the second container initially storing a dry medicament when the mixing and injector device is in the first stowed state, the actuation mechanism configured to selectively displace the liquid from the first container into the second container.

11. A mixing and injection system comprising:
a housing having a first container and a second container, where each container is separate and distinct from the other;
an actuation mechanism having a pre-stored energy source;
a needle assembly operatively connected to the second container,
wherein the needle assembly further comprises:
a needle,
a needle carrier carrying the needle, the needle carrier coupling the needle
to the second container, the needle carrier allowing for translation of the needle carrier and needle in an axial direction with
respect to the needle;
a septum configured to prevent fluid communication between the second container and the needle in a stowed state; and
wherein the needle penetrates the septum in an injection state.

12. The mixing and injector system of claim 11, further comprising:
a needle shield, the needle shield forming part of the actuation mechanism; and
wherein the needle shield operates as a bump trigger, the needle shield being operatively connected to the actuation mechanism such that upon depressing the needle shield against an injection site a portion of energy stored in the pre-stored energy source is discharged and pushes the needle carrier toward the injection site so as to abut against the needle shield, the discharged energy also causing the septum to drive against the proximal end of the needle thus causing the needle to penetrate the septum and allow displacement of the fluid contained within the plurality of containers through the needle.

13. The mixing and injector system of claim 11, wherein the needle carrier includes an engagement flange, and wherein at least one of the plurality of containers includes a septum protrusion housing the septum, the septum protrusion including a corresponding engagement flange configured to interface with the engagement flange of the needle carrier.

14. The mixing and injector system of claim 12, further comprising:
a septum protrusion provided about the second container;
wherein the needle carrier further comprises an engagement flange; and
wherein the septum protrusion includes a corresponding engagement flange configured to engage the septum protrusion in the stowed state.

15. The mixing and injector system of claim 13, wherein the engagement flange of the needle carrier is provided radially inward from an interior circumference of the needle carrier, and wherein the corresponding engagement flange of the septum protrusion is provided radially outwardly from an exterior circumference of the septum protrusion.

16. The mixing and injector system of claim 13, wherein a cross-sectional shape of the needle carrier coincides in shape with a cross-sectional shape of the septum protrusion, such that the septum protrusion nests within the needle carrier.

17. The mixing and injector system of claim 11, wherein a proximal end of the needle is initially embedded within the septum in a stowed state.

18. The mixing and injector system of claim 11, wherein the septum is configured to be pierced after the mixing and injector system is caused to enter a mixed state wherein a fluid which is initially stored in the first container is displaced from the first container and into the second container.

19. The mixing and injector system of claim 14, wherein first container initially stores a liquid when the mixing and injector device is in the stowed state, the second container initially storing a dry medicament when the mixing and injector system is in the stowed state, the actuation mechanism configured to selectively displace the liquid from the first container into the second container and subsequently from the second container through the needle.

20. A mixing and injection system comprising:
a housing having a first container and a second container;
an actuation mechanism having a pre-stored energy source;
a needle assembly operatively connected to the second container,
wherein the needle assembly further comprises:
a needle,
a needle carrier carrying the needle, the needle carrier having an engagement flange, and the needle carrier coupling the needle to the second chamber, the needle carrier allowing for translation of the needle carrier and needle in an axial direction with respect to the needle;
a septum protrusion provided about the second chamber, the septum protrusion including a corresponding engagement flange configured to engage with the engagement flange of the needle carrier, wherein the engagement flange of the needle carrier allows axial translation of the needle carrier along a length of the septum protrusion,
a septum provided within the septum protrusion being configured to prevent fluid communication between the second chamber and the needle in a stowed state, and
wherein the needle penetrates the septum in an injection state;
a needle shield, the needle shield forming part of the actuation mechanism;
wherein the first container initially stores a liquid when the mixing and injector device is in the stowed state, the second container initially storing a dry medicament when the mixing and injector system is in the stowed state, the actuation mechanism configured to selectively displace the liquid from the first chamber into the second container and subsequently from the second container through the needle;
wherein the needle shield operates as a bump trigger, the needle shield being operatively connected to the actuation mechanism such that upon depressing the needle shield against an injection site a portion of energy stored in the pre-stored energy source is discharged and pushes the needle carrier toward the injection site so as to abut against the needle shield, the discharged energy also causing the septum to drive against a proximal end of the needle thus causing the needle to penetrate the septum and allow displacement of the fluid contained within the plurality of containers through the needle; and wherein a cross-sectional shape of the needle carrier coincides in shape with a cross-sectional shape of the septum protrusion, such that the septum protrusion nests within the needle carrier.

* * * * *